United States Patent [19]

Fujita et al.

[11] Patent Number: 4,849,132
[45] Date of Patent: Jul. 18, 1989

[54] SURFACTANT COMPOSITION HAVING IMPROVED FUNCTIONS

[75] Inventors: Satoshi Fujita; Eiji Nakai, both of Tokyo; Akira Noike, Koshigaya, all of Japan

[73] Assignees: Asahi Denka Kogyo Kabushiki Kaisha, Tokyo; Nippon Shoji Kaisha, Ltd., Osaka, both of Japan

[21] Appl. No.: 48,013

[22] Filed: May 8, 1987

[30] Foreign Application Priority Data

| May 16, 1986 | [JP] | Japan | 61-113245 |
| May 16, 1986 | [JP] | Japan | 61-113246 |
| Jun. 18, 1986 | [JP] | Japan | 61-141624 |
| Jun. 18, 1986 | [JP] | Japan | 61-141625 |
| Jun. 18, 1986 | [JP] | Japan | 61-141627 |
| Jun. 18, 1986 | [JP] | Japan | 61-141628 |

[51] Int. Cl.$^4$ ............... B01F 17/34; B01J 13/00
[52] U.S. Cl. ............... 252/356; 252/174.17; 252/312; 426/654; 426/662
[58] Field of Search ............... 252/356, 174.17, 312; 426/662, 654

[56] References Cited

U.S. PATENT DOCUMENTS 4,115,313  9/1978  Lyon et al. .............. 252/309
4,681,617  7/1978  Ghyczy et al. .............. 252/356

OTHER PUBLICATIONS

Derwent Abstracts, AN 79-09069B/05, "Creamy Composition for Coffee", Japanese Patent, J53145960-A, 12/19/78.
Derwent Abstracts, AN 77-47993y/27, "Oil in Water Emulsion", Japanese Patent, J52063906, 5/26/77.
Derwent Abstracts, AN 74-55758v/31, "Foamy Cream Emulsifiers", J49015684, Japanese Patent, 2/12/74.

Primary Examiner—Paul Lieberman
Assistant Examiner—Christine A. Skane
Attorney, Agent, or Firm—Frishauf, Holtz, Goodman & Woodward

[57] ABSTRACT

The surfactant composition of the present invention, which comprises mono acyl glycero phosphilipid(s) and one or more compounds selected from the group consisting of polyglycerol fatty acid esters, sucrose fatty acid esters, sorbitan fitty acid esters and glycerol fatty acid monoesters as essential components, exhibits excellent acid- and salt-resistances, permeability, emulsification and dispersion capabilities and hydrophilicity. Further it is highly safe and can be appropriately applied to various products, in particular, food, cosmetics and pharamceuticals.

11 Claims, 2 Drawing Sheets

SURFACTANT COMPOSITION HAVING IMPROVED FUNCTIONS

BACKGROUND OF THE INVENTION

1. Field of the Invention

This invention relates to an improvement of surfactants available for various products including food and cosmetics. More particularly, it relates to an improvement of various surface activities of surfactants which are widely approved in many countries and highly safe when employed as materials for the production of, e.g., food, cosmetics and pharmaceuticals, i.e., polyglycerol fatty acid esters, sucrose fatty acid esters, sorbitan fatty acid esters and glycerol fatty acid monoesters.

2. Description of the Prior Art:

Polyglycerol fatty acids esters, which exhibit excellent biodegradabilities and approved to be safe, are widely employed in, for example, food and cosmetics as surfactants having various functions including emulsification, dispersion, solubilization, wetting and foaming, since they can show surface activities of a wide range hydrophile-lipophile balance (HLB) depending on the degree of polymerization and the type and number of the binding fatty acids.

Among these polyglycerol fatty acid esters, however, hydrophilic ones having an HLB of 13 or above would not give so stable emulsion of edible fats and oils as such and are thus unsuitable therefor, although they are soluble per se in acidic aqueous solutions or aqueous solutions of inorganic salts such as common salt. On the other hand, those having an HLB of 9 to 11 and generally used for emulsifying, for example, edible fats and oils and liquid paraffin are unstable to acidic aqueous solutions and aqueous solutions of inorganic salts such as common salt.

Further polyglycerol fatty acid esters having an HLB less than 9 are insoluble in acidic aqueous solutions and aqueous solutions of inorganic salts such as sodium chloride and inavailable in emulsifying edible fats and oils as such.

The wetting, solubilization and dispersion capabilities, which are important properties of surfactants, of polyglycerol fatty acid esters are lower even in the case of hydrophilic ones than other surfactants. For example, the permeation capabilities of the same are lower than those of sucrose fatty acid esters and thus, needless to say, much lower than those of a polyoxyethylene alkylphenol ethers.

Sucrose fatty acid esters, which exhibit excellent biodegradabilities and are approved as safe, are widely employed in, for example, food and cosmetics as surfactants having various functions such as emulsificaiton, dispersion, solubilization, permeation and foaming since they can show surface activities of a wide range of HLB depending on the type and number of the fatty acids bound to sucrose.

However these sucrose fatty acid esters, which are nonionic surfactants, are readily precipitated in acidic aqueous solutions and aqueous solutions of inorganic salts such as common salt, which lowers the surface activities thereof. Although sucrose fatty acid esters containing monoesters in an amount of almost 100%, in particular those which are monoesters of short-chain or unsaturated fatty acids, are relatively stable in acidic aqueous solutions or aqueous solutions of inorganic salts, they are extremely expensive and can not be employed in practice.

Thus most of commercially available sucrose fatty acid esters have a disadvantage that they would almost lose the surface activities at a pH value of 4 to 6 or at a common salt concentration of 1%. There are many aqueous solutions of, for example, food products having pH values or common salt concentrations within the ranges as described above. Therefore the above disadvantage of sucrose fatty acid esters strictly limits the application of the same.

In addition, the permeation capability, i.e., wetting power, which is one of the surface activities, of a sucrose fatty acid ester having a high HLB is insufficient when compared with that of, for example, a polyoxyethylene alkylphenol ether.

Sorbitan fatty acid esters are esters of one or more compounds selected from among sorbitol, sorbitan and sorbide, the latter two being intramolecularly dehydrated products of the former, with a fatty acid. They can exhibit surface activities of a relatively lipophilic HLB depending on the type and number of the binding fatty acids. They are widely used in various products including food and cosmetics as surfactants, mainly as an emulsifiers, which show excellent biodegradabilities and are approved as safe.

However sorbitan fatty acid esters generally show poor solubilities in water. In particular, they are apt to be readily precipitated in acidic aqueous solutions of, for example, a pH value of 5 to 6 or aqueous solutions of inorganic salts such as sodium chloride at a concentration of, for example, 1%, which lowers the surface activities thereof.

There are many aqueous solutions of, for example, food products having pH values or common salt concentrations within the ranges as defined above. Thus the above disadvantage of sorbitan fatty acid esters strictly limits the application of the same.

In addition, the wetting and dispersion capabilities, which are important surface activities, of sorbitan fatty acid esters are very poor.

Glycerol fattly acid monoesters, which are natural surfactants present in living organisms, are produced through transesterification between fats or oils and glycerol or reactions between fatty acids and glycerol. Since these glycerol monoesters have simple structures, they can be readily purified to a high purity by distillation. Thus they are useful surfactants and available at a relatively low price. However the glycerol monoesters are highly lipophilic and insoluble in water. Those containing a large amount of impurities including fatty acid soaps can be dispersed in hot water but would cause phase separation at room temperature, which strictly limits the application of the same.

SUMMARY OF THE INVENTION

It is an object of the present invention to provide a surfactant composition having improved properties including acid—and salt—resistances, wetting, emulsification and dispersion capabilities and hydrophilicity by overcoming the abovementioned disadvantages of polyglycerol fatty acid esters, sucrose fatty acid esters, sorbitan fatty acid esters and glycerol fatty adic monoesters. The composition of the present invention comprises the following compounds as essential components:

A. mono acyl glycero phospholipids; and

B. one or more compounds selected from the group consisting of polyglycerol fatty acid esters, sucrose fatty acid esters, sorbitan fatty acid esters and glycerol fatty acid monoesters.

DETAILED DESCRIPTION OF THE PRESENT INVENTION

The mono acyl glycero phospholipids, which are the first essential component of the composition of the present invention, are preferably those having eight or more carbon atoms. In each mono acyl glycero phospholipid, the acyl group may be located in either $\alpha$- or $\beta$-position. As the mono acyl glycero phospholipids, both of natural ones of L-form and synthetic racemates may be used.

It is known that natural mono acyl glycero phospholipids are present in living organisms together with acyl glycero phospholipids in, for example, lipids of cereals such as soybean, rapeseed and wheat and animal lipids. Mono acyl glycero phospholipids may be further produced by hydrolyzing diacyl glycero phospholipid present in animal lipids such as yolk or vegetable lipids such as soybean with phospholipase A-2 obtained from swine pancreatic juice of snake venom or phospholipase A-1 obtained from bacteria; removing the fatty acids thus formed with, for example, acetone; and purifying the residue by, for example, silica gel chromatography, if required (cf. Japanese Patent-Laid Open No. 13263/1971, No. 136966/1977 and No. 51853/1983). In this case, the mono acyl glycero phospholipid thus obtained may be hydrogenated in an appropriate solvent in the presence of a catalyst such as nickle to thereby give a surfactant having a higher oxidation stability.

It is described in J. Amer. Oil Chem. Soc., 886–888, Oct. 1981 that mono acyl glycero phospholipids of various compositions can be obtained by changing the conditions under which the phospholipase A-2 is employed.

Alternately, mono acyl glycero phospholipids can be obtained from materials prepared by fractionating diacyl glycero phospholipids with the use of a solvent such as ethyl alcohol, and/or water containg ethyl alchohol. Further methods for preparing mono acyl glycero phospholipids such as the one for preparing phosphatidylcholine from yolk (cf. J. Biol. Chem., 188, 471–476 (1951) as well as those for preparing phosphatidylcholine as described in Japanese Patent Publication No. 16/1985, No. 42655/1984, No. 123496/1982 and No. 23997/1981 can be applied to the present invention. Every natural mono acyl glycero phospholipid as mentioned above has a levo-rotatory optical activity and is turned out to be safe when orally administered to animals (cf. J. Sci. Food and Agr., 32, 451–458).

The phospholipids as used in the present invention can be analyzed by, for example, thin layer chromatography, TLC - FID Analyser (Iatro - scan method) or high performance lilquid chromatography.

It is preferable that the mono acyl glycero phospholipids (a) to be used in the present invention, which can be obtained by the methods as described above, substantially comprise mono acyl phosphatidylcholine. The mono acyl glycero phospholipids (a) may further contain mono acyl phosphatidylethanolamine and a small amount of one or more mono acyl phoslpholipids selected from among mono acyl phosphatidylinositol, mono acyl phosphatidic acid and mono acyl phosphatidylserine. The mono acyl glycero phospholipids (a) prepared from natural materials often contain diacyl phosphatides (b) corresponding to the mono acyl glycero phospholipids (a) depending on the employed preparation processes. In such a case, the desired effects can be achieved under strongly acidic conditions or at a high concentration of a salt so long as the content of the mono acyl glycero phospholipids (a) is 30% by weight or above based on the total phosphatides, i.e., (a)+(b). However it is preferable that the content of the mono acyl glycero phospholipids (a) is 40% by weight or above when the mono acyl glycero phospholipids contain mono acyl glycero lysophosphatidylcholine in a low amount, for example, 60% by weight or below.

Generally speaking, the required amount of the mono acyl glycero phospholipids would be lowered with an increase in the content of the same.

Now the fatty acid esters, which are another essential component of the composition of the present invention, will be described.

As the polyglycerol fatty acid esters which are the essential component of the composition of the present invention, mono-, di- or polyesters of polyglycerols having a degree of polymerization of 4 to 12 with saturated and/or unsaturated fatty acids having 12 to 22 carbon atoms and mixtures thereof are preferable. Polyglycerol fatty acid esters comprising fatty acids having 11 or less carbon atoms would exhibit a bitter taste and only limited effects of the addition of the mono acyl glycero phospholipids of the present invention, e.g., the emulsification and dispersion capabilities can be achieved thereby. On the other hand, those comprising fatty acids having 23 or more carbon atoms are hardly available in general. A degree of polymerizaiton of polyglycerol less than 4 would result in only insufficient hydrophilicity, while that more than 12 is undesirable since complicated polymerizaation is liable to occur in each molecule.

Examples of the sucrose fatty acid esters constituting the second essential component of the composition of the present invention are mono-, di- or polyesters of saturated and/or unsaturated fatty acids having 12 to 22 carbon atoms with sucrose and mixtures thereof. Sucrose fatty acid esters comprising fatty acids having 11 or less carbon atoms would exhibit a bitter taste and only limited effects of the addition of the mono acyl glycero phospholilpids of the present invention can be achieved thereby. On the other hand, those comprising fatty acids having 23 or more carbon atoms are hardly available in general.

Examples of the sorbitan fatty acid esters constituting the second essential component of the composition of the present invention are mono-, di- or polyesters of saturated and/or unsaturated fatty acids having 12 to 22 carbon atoms with sorbitol, sorbitan and sorbide and mixtures thereof. Only limited emulsification effects of the addition of the mono acyl glycero phospholipids of the present invention can be achieved with the use of sorbitan fatty acid esters comprising fatty acids having 11 or less carbon atoms. On the other hand, those comprising fatty acids having 23 or more carbon atoms are hardly available in general.

Examples of the glycerol fatty acid monoesters constituting the second essential component of the composition of the present invention are monoesters of saturated and/or unsaturated fatty acids having 12 to 22 carbon atoms with glycerol and mixtures mainly comprising the monoesters together with diesters. Glycerol fatty acid monoesters comprising fatty acids having 11 or less carbon atoms would give bitter taste and insufficient emulsifying ability and thus hardly contribute to an improvement in the properties of the composition. On the other hand, those comprising fatty acids having 23 or more carbon atoms are hardly available in general.

A glycerol fatty acid monoester comprising both the monoester and the diesters preferably contain 70% by weight or more, still preferably 80% by weight or more, of the monoester. It is desirable to use a distilled product.

It is preferable that the composition of the present invention comprises polyglycerol fatty acid ester(s), sucrose fatty acid ester(s), sorbitan fatty acid ester(s) and glycerol fatty acid monoesters and mono acyl glycero phospholipid(s) at a ratio of 10/90 to 95/5 on a weight basis.

When it comprises mono acyl glycero phospholipid(s) in an amount of 5% or less, only limited effects of the present invention may be achieved. On the other hand, the content of the mono acyl glycero phospholipid(s) of 90% or above therein makes the composition undesirably expensive.

When the composition of the invention comprises polyglycerol fatty acid ester(s) of an HLB of 11 or above, sufficient effects can be achieved even when the content of mono acyl glycero phospholipid(s) is relatively low. On the contrary, when polyglycerol fatty acid ester(s) have a low HLB and the mono acyl glycero phospholipid(s) are contained in a proportion of 5 to 10%, the effects of the present invention can be observed in a relatively dilute aqueous solution of sodium chloride or at only a relatively high pH value acidic solution. Therefore, it is preferable that the mono acyl glycero phospholipid(s) are contained in a proportion of 10% or above. When the composition of the present invention comprises polyglycerol fatty acid ester(s), the effects of the invention show little difference at contents of mono acyl glycero phospholipid(s) of approximately 60% or above. Thus it is generally preferable that the mono acyl glycero phospholipid(s) are contained at a ratio of 40/60 to 90/10 (these ratio shows Poly glycero fatty ester/mono acyl glycero phospholipid still preferably approximately 40/60 to 95/5 at a case polyglycerol fatty acid ester having high HLB.

Generally speaking, the required amount of mono acyl glycero phospholipid(s) would decrease with an increase in the HLB of polyglycerol fatty acid ester(s).

When the composition of the present invention comprises sucrose fatty acid ester(s), the effects of the present invention can be observed in a relatively dilute aqueous solution of common salt or at only a relatively high pH value in acidic solution at a mono acyl glycero phospholipids content of 5 to 10%. Therefore it is preferable that the mono acyl glycero phospholipid(s) are contained at a content of 10% or above. Similar to the case of polyglycerol fatty acid esters, the effects of the present invention show little difference at contents of mono acyl glycero phospholipid(s) of approximately 60% or above in the case of sucrose fatty acid esters. Thus it is generally preferable that the mono acyl glycero phospholipid(s) are contained at a ratio of approximately 40/60 to 90/10.

Generally speaking, the required amount of mono acyl glycero phospholipid(s) would decrease with an increase in the HLB of sucrose fatty acid ester(s).

When the composition of the present invention comprises sorbitan fatty acid ester(s), the effects of the present invention can be observed in a relatively dilute aqueous solution of sodium chloride or at only a relatively high pH value in a acidic solution at a mono acyl glycero phospholipids content of 5 to 20%. Thus it is preferable that mono acyl glycero phospholipid(s) are contained at a proportion of 20% or above. Similar to the former cases, the effects of the present invention show little difference at contents of mono acyl glycero phospholipid(s) of approximately 60% or above in the case of sorbitan fatty acid esters. Thus it is generally preferable that the mono acyl glycero phospholipid(s) are contained at a ratio of approximately 40/60 to 80/20.

Generally speaking, the required amount of mono acyl glycero phospholipid(s) would decrease with an increase in the HLB of sorbitan fatty acid ester(s).

When the composition of the present invention comprises glycerol fatty acid monoester(s), the effects of the present invention can be observed in a relatively dilute aqueous solution of common salt or at a relatively high pH value in a acidic solution at a mono acyl glycero phospholipids content of 5 to 10%. Thus it is preferable that mono acyl glycero phospholipid(s) are contained at a proportion of 10% or above. The compositional ratio varies depending on the purpose. For example, when the composition is used for water-in-oil type and oil-in-water type emulsification, compositional ratios of approximately 80/20 (glycerol fatty acid mono ester/mono acyl glycero phospholipids) to 90/10 and approximately 10/90 to 80/20 are preferable, respectively. When it is to be used under severe conditions such as at pH 3 or in a 10% by weight saline solution, a compositional ratio of 10/90 to 70/30 is preferable. Under particularly severe conditions such that corn oil is to be emulsified in soy sauce, a compositional ratio of 10/90 to 50/50 is preferable.

The composition of the present invention can be obtained by, for example, the following methods.

(1) Mono acyl glycero phospholipid(s) and each fatty acid ester are formulated into each an aqueous solution or an aqueous paste.

(2) Each aqueous solution ro aqueous paste as prepared above in (1) is further concentrated in vacuo to give a semisolid or solid products.

(3) When both of the mono acyl glycero phospholipid(s) and fatty acid ester are solid, they are formulated into powders and mixed together.

(4) Mono acyl glycero phospholipid(s) and each fatty acid ester are dissolved in a solvent such as an alcohol or hexane or a mixture thereof.

(5) The solution obtained above in (4) is dried to give a powder or a paste.

(6) In the case of some polyglycero fatty acid ester and glyceryl fatty acid mono ester, these materials are heated together with mono acyl glycero phospholipid(s) under stirring at the melting points or above to thereby melt these materials together.

The composition of the present invention may further contain other surfactants without departing from the scope thereof.

It is further preferable that the composition of the present invention also contains soluble proteins, peptides and polysaccharides since these materials would enhance the emulsification, solubilization and dispersion capabilities of the former.

The surfactant composition of the present invention can be applied to various products containing inorganic salts and/or organic acids, for example, soy sauce, worcester sauce, pickled vegetables such as salted ones and those pickled in soy sauce, fruit juices, fermented milk products such as yoghurt, dressing, mayonnaise, tsukudani, processed animal and fish meats and cosmetics. It is effective in emulsifying oily materials; solubilizing oily colorants, oil soluble vitamins and antioxidants such as BHA and BHT; and dispersing cocoa powder, powdery precooked foods, spices such as powdery mustard or horseradish, fungicides such as butyl p-hydroxybenzoate and various powdery additives. Alternately the composition of the present invention may be dissolved in water or alcohols and the obtained solution is allowed to adhere to particles to be dispersed by immersing or spraying to thereby coat the particles with the solution, thus accelerating the dispersion of the powder.

EXAMPLES

To further illustrate the present invention, and not by way of limitation, the following Examples will be given.

Preparation of mono acyl glycero phospholipid:

Now the mono acyl glycero phospholipids to be used in the present invention will be described in detail.

Mono acyl glycero phospholipid A:

Phospholipids containing 70% of diacyl phosphatidylcholine are obtained from commercially available soybean phospholipids through precipitation with acetone and fractionation with aqueous ethanol. Then phospholipase A obtained from swine pancreatic juice (Lecitase 10-L mfd. by Novo) is added thereto. The fatty acids thus formed are removed with the use of acetone and the residue is fractionated with an alcohol. After further fractionating with the use of a silicic acid column and an alcohol, the title material, which is a phosphatide comprising 94% of lyso phosphatidylcholine and 3% of lyso phosphatidylethanolamine, is obtained.

Mono acyl glycero phospholipid B:

Starting from commercially available soybean phospholipids, the procedure as described in regard to mono acyl glycero phospholipid A is followed to thereby give the title material which is a phosphatide comprising 95% of lyso phosphatidylcholine and 2% of lysophasphatidylethanolamine.

Mono acyl glycero phospholipid C:

Phospholipids containing 70% of di acyl phosphatidylcholine are obtained by fractionating soybean phospholipids. Then Lecitase 10-L is added thereto and the fatty acids thus formed are removed. The residue is fractionate with an alcohol and purified to give the title material which is a phospholipid mainly comprising 56% of lyso phosphatidylcholine and 13% of lyso phosphatidylethanolamine and containing 72% of mono acyl glycero phospholipids in total.

Mono acyl glycero phospholipid D:

Lecitase 10-L is added to defatted phospholipids obtained by precipitating commercially available soybean phospholipids with the use of acetone. Then a phosphatide is extracted with a mixture of isopropyl alcohol and hexane and treated with acetone to thereby defat the same. Then it is extracted with an alcohol to give the title material which is a phosphatide comprising 52% of lyso phosphatidylcholine and 11% of lyso phosphatidylethanolamine and containing 65% of mono acyl glycero phospholipids in total.

Mono acyl glycero phospholipid E:

Defatted phospholipids are obtained from soybean phospholipids through precipitation with acetone. Then Lecitase 10-L is added thereto and a phosphatide is extracted with a mixture of isopropyl alcohol and hexane and treated with acetone to thereby defat the same. After extracting an alcohol, the title material, which is phosphatide mainly comprising 52% of lyso phosphatidylcholine and 14% of lyso phosphatidylethanolamine and containing 69% of mono acyl glycero phospholipids in total, is obtained.

Mono acyl glycero phospholipid F:

Defatted phospholipids are obtained from soybean phospholipids through precipitation with acetone. Then Lecitase 10-L is added thereto and a phosphatide is extracted with a mixture of isopropyl alcohol and hexane and treated with acetone to thereby defat the same. After extracting with an alcohol, the title material, which is a phosphatide mainly comprising 45% of lyso phosphatidylcholine and 9% of lyso phosphatidylethanolamine and containing 56% of mono acyl glycero phospholipids in total, is obtained.

Mono acyl glycero phospholipid G:

Lecitase 10-L is reacted with Lecinol 10-E (mfd. by Nippon Surfactant Co., Ltd.; a hydrogenated phosphatide containing 81% of phosphatidylcholine and 9% of phosphatidylethanolamine and having an iodine value of (7) and the reaction mixture is treated in the same manner as the one described in the case of mono acyl glycero phosphatide D. Thus the title material, which is a phosphatide mainly comprising 69% of lyso phosphatidylcholine and 8% of lyso phosphatidylethanolamine and containing 80% of mono acyl glycero phospholipids in total, is obtained.

Mono acyl glycero phospholipid H:

Defatted phospholipids are obtained from soybean phospholipids through precipitation with acetone. Then Lecitase 10-L is added thereto and a phosphatide is extracted with a mixture of isopropyl alcohol and hexane. After removing the solvent from the extract, fatty acids are removed therefrom by treating with acetone and the residue is further extracted with an alcohol. Thus the title material, which is a phosphatide mainly comprising 48% of lyso phosphatidylcholine and 11% of lyso phosphatidylethanolamine and containing 62% of mono acyl glycero phospholipids in total, is obtained.

Mono acyl glycero phospholipid J:

Lecitase 10-L is reacted with Lecinol 10 E (mfd. by Nippon Surfactant Co., Ltd.; a hydrogenated phosphatide containing 81% of phosphatidylcholine and 9% of phosphatidylethanolamine and having an iodine value of (7) and the reaction mixture is treated in the same manner as described with regard to mono acyl glycero phospholipid H. Thus the title material, which is a phosphatide mainly comprising 53% of lyso phosphatidylcholine and 5% of lyso phosphatidylethanolamine and containing 61% of mono acyl glycero phospholipids in total, is obtained.

Mono acyl glycero phospholipid K:

Epicuron 200 (mfd. by Lucas Meyer) containing 94% of phosphatidylcholine and prepared from soybean phospholipids is dispersed in water and reacted with Lecitase 10-L. After removing fatty acids with acetone, the title material, which is a phosphatide mainly comprising 38% of lyso phosphatidylcholine and containing 39% of mono acyl glycero phospholipids in total, is obtained.

Mono acyl glycero phospholipid L:

Soybean phospholipids are treated with acetone and then with ethanol and treated in the same manner as the one described with regard to mono acyl glycero phospholipids B to thereby give a phosphatide containing 70% by weight of diacyl phosphatidylcholine. This phosphatide is dispersed in water and reacted with Lecitase 10-L. Fatty acids are removed from the reaction mixture with the use of acetone. Thus the title material, which is a phosphatide mainly comprising 31% of lyso phosphatidylcholine and 4% of lyso phosphatidylethanolamine and containing 36% of mono acyl glycero phospholipids in total, is obtained.

Mono acyl glycero phospholipids M:

Soybean phospholipids are treated with acetone and reacted with Lecitase 10-L. Then fatty acids are removed therefrom by adding acetone thereto again followed by drying. Thus the title material, which is a phosphatide mainly comprising 24% of lyso phosphatidylcholine and 8% of lyso phosphatidylethanolamine and containing 37% of mono acyl glycero phospholipids in total, is obtained.

In the following Examples, the content (%) of mono acyl glycero phospholipid(s) in each aqueous paste, which contained the composition of the present invention and was subjected to each test, is expressed on an absolute basis based on the total amount of the first and second components, i.e., polyglycerol fatty acid ester(s), sucrose fatty acid ester(s), sorbitan fatty acid ester(s) and glycerol fatty acid monoesters and the mono acyl glycero phospholipid(s). The term "phosphatide" as used herein means a composition containing mono acyl glycero phospholipid(s) and diacyl phosphatide(s), while the term "glycerol fatty acid ester" as used herein means a composition containing glycerol fatty acid monoester(s) and glycerol fatty acid diester(s).

EXAMPLE 1

Mono acyl glycero phospholipid A and a polyglycerol fatty acid ester (Sun Soft Q-17-U mfd. by Taiyo Kagaku Co., Ltd.; decaglycerol monooleate having an HLB 15 were mixed at various weight ratios and each mixture thus obtained was formulated into an aqueous paste containing 50% by weight of the composition of the present invention.

(1) Emulsification stability test on corn salad oil and aqueous solution of common salt 0.8 g of each paste, 40 g of corn salad oil and 60 ml of an 8% of aqueous solution of common salt were emulsified in a turbotype homogenizer (AM-8 mfd. by Nippon Seiki Co., Ltd.) at 55° C. and 12,000 rpm for five minutes. The emulsion thus formed was introduced into a glass cylinder and stored in an incubator at 40° C. under observation.

In the case of the composition comprising the polyglycerol fatty acid ester alone, 9% of an oily phase separated out after 30 days. On the other hand, in the cases of those containing 5%, 10% and 40% of the mono acyl glycero phospholipid, 5%, 3% and 2% of oily phases separated out respectively.

(2) Emulsification stability test on corn salad oil and soy sauce 1 g of each paste, 50 g of corn salad oil and 50 g of "Koikuchi" soy sauce (having 15 wt% sodium chrolide; mfd by Kikkoman Co., Ltd.) were emulsified in a homogenizer (AM-8) at 55° C. and 13,000 rpm of six minutes. The emulsion thus formed was introduced into a glass cylinder and stored in an incubator at 40° C. under observation.

In the case of the composition comprising the polyglycerol fatty acid ester alone, 11% of an oily phase separated out after 30 days. On the other hand, in the cases of those containing 5%, 20% and 40% of the mono acyl glycero phospholipid, 7%, 4% and scarcely any oily phases separated out respectively.

(3) $\beta$-Carotene solubilization test 1 g of each paste was dissolved in water to give a volume of 50 ml. 10 ml of the aqueous solution thus obtained and 10 mg of powdery $\beta$-carotene were introduced into a 30-ml test tube and shaken at 30° C. for 42 hours to thereby solubilize the $\beta$-carotene. The solubilized product was then centrifuged at 3,000 rpm. To 2 ml of the supernatant, 8 ml of a mixture of chloroform and ethanol (1:4) was added and the absorbance of the resulting mixture was determined at 455 nm with a spectrometer, The composition comprising the polyglycerol fatty acid ester alone showed an absorbance of 0.041 while the one comprising the mono acyl glycero phospholipid alone showed that of 0.372. On the other hand, those comprising 10%, 25% and 50% of the mono acyl glycero phospholipid showed absorbances of 0.394, 0.898 and 0.876, respectively.

(4) Surface activity test 2.5 of each paste was dissolved in water to give a volume of 250 ml. The surface tension of the obtained aqueous solution was determined with a surface tension meter at 25° C. (CBVP A-3; mfd. by Kyowa Kagaku Co., Ltd.) and the permeation power (this means wettability) thereof was determined according to Kimura's canvas disc method at 25° C.

The composition comprising the polyglycerol fatty acid ester alone showed a surface tension of 33.4 dyne/cm and a permeation period (this means wetting time) of 15 minutes and 18 seconds. On the other hand, those containing 5%, 10% and 40% of the mono acyl glycero phospholipids showed surface tensions of 33.1 dynes/cm, 32.3 dyne/cm and 32.5 dyne/cm, respectively, and permeation period of 7 minutes and 6 seconds, 4 minutes and 6 seconds, and 2 minutes and 54 seconds, respectively.

(5) Emulsification test on corn salad oil and grapefruit juice 1 g of each paste was dissolved in water to give a volume of 25 ml. 10 ml of the obtained aqueous solution, 20 ml of corn salad oil and 70 ml of reconstituted grapefruit juice (pH 3.3) were mixed together and the obtained mixture was emulsified at 60° C. in the same manner as the one described with regard to the emulsification stability test on corn salad oil and aqueous solution of common salt. The obtained emulsion was stored at 40° C. under observation.

In the case of the composition comprising the polyglycerol fatty acid ester alone, 4% of an oily phase separated out after 30 days. On the other hand, in the case of those containing 10% and 20% of teh mono acyl glycero phospholipids, 1% and scarcely any oily phases separated out.

EXAMPLE 2

Mono acyl glycero phospholipid A and a polyglycerol fatty acid ester having a HLB 10 (SY Glyster SS-500 mfd. by Sakamoto Yakuhin Co., Ltd.; mainly comprising stearic acid and having a degree of polymerization of polyglycerol of 6 and having an HLB 10) were mixed at various weight ratios and each mixture thus obtained was formulated into a 25% by weight aqueous paste.

(1) Acid- and salt-resistance test 1 g of each paste was dissolved in water to give a volume of 25 ml. To one-part portions of the aqueous solution thus obtained, one-part portions of water, a 0.2M phthalate buffer solution of pH 3 and a 20% aqueous solution of common salt were added to respectively give a control solution, an acidic solution and a saline solution and each solution was heated to 60° C. for ten minutes and allowed to stand, and the transmittance was determined at 720 nm after one day.

In the case of the composition comprising the polyglycerol fatty acid ester alone, the control solution showed a transmittance of 32% while the acidic and saline solutions showed separation of the surfactant. In the case of the composition comprising 20% of the mono acyl glycero phospholipid, the control solution and the acidic solution showed transmittances of 94% and 82%, respectively. In the case of the composition comprising 30% of the same, the control solution, the acidic solution and the saline solution showed transmittances of 98%, 95% and 81%, respectively. In the cases of those comprising 40% or more of the same, no difference was observed among the control, acidic and saline solutions.

(2) Emulsification stability test on corn salad oil and aqueous solution of common salt With the use of 1.6 g of each paste, 40 g of corn salad oil and 59 ml of an aqueous solution of common salt, the procedure of Example 1 was followed. As a result, 14% of an oily phase separated out after 30 days in the case of the composition comprising the polyglycerol fatty acid ester alone. On the other hand, 1% of an oily phase separated out in the case of the composition comprising 10% of the mono acyl glycero phospholipid while scarcely any separation was observed in the case of those comprising 40% or more of the same.

(3) Emulsification stability test on corn salad oil and soy sauce

The procedure of Example 1 was followed with the use of 2 g of each paste, 50 g of corn salad oil and 55 g of "Koikuchi" soy sauce. In the case of the composition comprising the polyglycerol fatty acid ester alone, 5% of an oily phase consequently separated out after 30 days. In the case of the composition comprising 10% of the mono acyl glycero phospholipid, 1% of an oily phase separated out while scarcely any separation was observed in the cases of those comprising 20% or more of the same.

(4) Emulsification test on corn salad oil and grapefruit juice

The procedure of Example 1 was followed with the use of 2 g of each paste. In the case of the composition comprising the polyglycerol fatty acid ester alone, 2% of an oily phase consequently separated out after 20 days. On the other hand, scarcely any separation was observed in the cases of those comprising 10% or more of the same.

EXAMPLE 3

Mono acyl glycero phospholipid A and a polyglycerol fatty acid ester of an HLB of 11 (SY Glyster MO-500 mfd. by Sakamoto Yakuhin Co., Ltd.; mainly comprising oleic acid and having a degree of polymerization of polyglycerol of (6) were mixed together at various weight ratios and each mixture thus obtained was formulated into a 20% by weight aqueous paste.

(1) Surface activity test 5 g of each paste was dissolved in 200 ml of water and subjected to the same test as the one described in Example 1. As a result, the composition comprising the polyglycerol fatty acid ester alone showed a surface tension of 35.0 dyne/cm and a permeation period of 18 minutes and 18 seconds. On the other hand, those comprising 10%, 20% and 40% of the mono acyl glycero phospholipid showed surface tensions of 33.9 dynes/cm, 32.8 dynes/cm and 32.3 dynes/cm, respectively, and permeation periods of 7 minutes and 12 seconds, 4 minutes and 54 seconds and 3 minutes and 24 seconds, respectively.

EXAMPLE 4

Mono acyl glycero phospholipid D and Sun Soft Q-17-U were mixed together at various weight ratios and each mixture thus obtained was formulated into a 50% by weight aqueous paste.

(1) Surface activity test

The procedure of Example 1 was follwed. As a result, the composition comprising the polyglycerol fatty acid ester alone showed a surface tension of 33.4 dynes/cm and a permeation period of 15 minutes and 20 seconds. On the other hand, those comprising 6%, 13% and 29% of the mono acyl glycero phospholipid showed surface tensions of 31.7 dynes/cm, 30.2 dynes/cm and 29.6 dynes/cm, respectively, and permeation periods of 4 minutes and 6 seconds, 2 minutes and 54 seconds and 2 minutes and 18 seconds, respectively.

(2) Emulsification stability test on corn salad oil and soy sauce

The procedure of Example 1 was follwed. In the case of the composition comprising the polyglycerol fatty acid ester alone, 11% of an oily phase seperate out after 30 days. In the cases of those comprising 6% and 2% of the mono acyl glycero phospholipid, 6% and 13% of oily phases separated out while scarcely any separation was observed in the cases of those comprising 29% or more of the same.

(3) β-Carotene solubilization test

The procedure of Example 1 was follwed. As a result, the composition comprising the polyglycerol fatty acid ester alone showed an absorbance of 0.041. On the other hand, those comprising 15% and 38% of the mono acyl glycero phospholipid showed absorbances of 0.277 and 0.512, respectively.

(4) Dispersion test on fine inorganic particles 1 g of each paste was dissolved in water to give a volume of 250 ml. 20 ml of the obtained aqueous solution and 1 g of a titanium white pigment were introduced into a Nessler tube and vigorously shaken vertically to thereby disperse the pigment in the solution. After adding 5 ml of a 30% aqueous solution of common salt thereto, the mixture was shaken again and allowed to stand in room temperature under observing the dispersion and sedimentation condition.

As a result, the composition comprising the polyglycerol fatty acid ester alone showed aggregation and sedimentation after 20 minutes regardless of the addition of the common salt solution. In contrast, thereto, that comprising 10% of the mono acyl glycero phospholipid showed little sedimentation after one hour and those comprising 24% or more of the same showed stable dispersion after three hours.

A similar test was carried out with the use of highly fine grains of calcium carbonate. As a result, the composition comprising the polyglycerol fatty acid ester alone immediately showed aggregation and sedimentation while those comprising 15% or more of the mono acyl glycero phospholipid showed stable dispersion after three hours.

(5) Emulsification test on corn salad oil and grapefruit juice

The procedure of Example 1 was followed. As a result, the compositions comprising 6% or more of the mono acyl glycero phospholipid showed scarcely any phase separation after 20 days while 2% of an oily phase separated out in the case of the composition comprising no mono acyl glycero phospholipid.

EXAMPLE 5

Mono acyl glycero phospholipid F and SY Glyster MO-500 were mixed together at various weight ratios and each mixture thus obtained was formulated into a 50% by weight aqueous paste.

(1) Emulsification stability test on corn salad oil and soy sauce

The procedure of Example 1 was followed. In the case of the composition comprising the polyglycerol fatty acid ester alone, 2% of an oily phase consequently separated out. On the other hand, scarcely any separation was observed after a month in the cases of those comprising 5.3%, 11% and 25% of the mono acyl glycero phospholipid.

(2) Surface activity test

The procedure of Example 1 was followed. As a result, the composition comprising the polyglycerol fatty acid ester alone showed a surface tension of 35.9 dyne/cm and a permeation period of 18 minutes and 18 seconds. On the other hand, those comprising 5.3%, 11% and 25% of the mono acyl glycero phospholipid showed surface tensions of 35.5 dyne/cm, 34.9 dyne/cm and 34.3 dyne/cm, respectively, and permeation periods of 7 minutes and 12 seconds, 5 minutes and 6 seconds and 3 minutes and 10 seconds, respectively.

EXAMPLE 6

Mono acyl glycero phospholipid G and Sun Soft Q-17-U were mixed together at various weight ratios and each mixture thus obtained was formulated into a 50% by weight aqueous paste.

(1) Emulsification stability test on corn salad oil and soy sauce

The procedure of Example 1 was followed. In the case of the composition comprising the polyglycerol fatty acid ester alone, 11% of an oily phase separated out after 30 days and a number of giant oil droplets of several millimeters in diameter were observed in a creaming phase, suggesting that the emulsion was broken. In contrast thereto, 2% of an oily phase separated out in the case of the composition comprising 17% of the mono acyl glycero phospholipid and scarcely any separation was observed even after one month of the cases of those comprising 26% or more of the same.

EXAMPLE 7

60 parts by weight of SY Glyster MO-500 and 40 parts by weight of mono acyl glycero phospholipid D were dissolved in 900 parts by weight of ethanol.

50 g of the solution thus obtained was mixed with 500 g of a alkali treated cocoa powder containing 23% of fat in a Kenwood mixer under stirring and the resulting mixture was dried in vacuo and ground to thereby give an instant cocoa.

2 g of this instant cocoa was suspended on 100 ml of water and the period required for the sedimentation of the whole produce was determined. As a result, the above cocoa required 3 minutes and 42 seconds for the sedimentation while a comparative product comprising the polyglycerol fatty acid ester alone required 17 minutes and 36 seconds therefor.

EXAMPLE 8

Mono acyl glycero phospholipid B and a polyglycerol fatty acid ester havign an HLB of 8 (SY Glyster MS-310 mfd. by Sakamoto Yakuhin Co., Ltd.; mainly comprising stearic acid and having a degree of polymerization of polyglycerol of (4) were mixed together at various weight ratios and each mixture thus obtained was formulated into an aqueous paste containing 25% by weight of solids.

(1) Acid- and salt-resistance test

The procedure of Example 2 was followed with the use of aqueous solutions prepared by dissolving 4 g of each paste in water to give a volume of 200 ml and the transmittance of each sample was determined at 720 nm.

As a result, in the case of the composition comprising the polyglycerol fatty acid ester alone, the control solution showed a transmittance of 8% and the acidic and saline solutions showed separation of the surfactant. On the other hand, in the case of the composition comprising 30% of the mono acyl glyceo phospholipid, the control, acidic and saline solutions showed transmittance of 82%, 75% and 79%, respectively. Little difference was observed among the transmittances of the control (87%), acidic and saline solutions in those comprising 40% or more of the same.

(2) Emulsification stability test on corn salad oil and soy sauce 2 g of each paste, 50 g of corn salad oil and 56 g of "Koikuchi" soy sauce were emulsified in a turbo type homogenizer (AM-8 mfd. by Nippon Seiki Co., Ltd.) at 55° C. and 13,000 rpm for 6 minutes. The obtained emulsion was introduced into a glass cylinder and stored in an incubator while periodically changing the temperature, i.e., at 20° C. for 8 hours and at 40° C. for 16 hours.

In the case of the composition comprising the polyglycerol fatty acid ester alone, 8% of an oily phase consequently separated out after 30 days. On the other hand, 2% of an oily phase separated out in the case of the composition comprising 10% of the mono acyl glycero phospholipid and scarcely any separation was observed after 60 days in the cases of those comprising 20% or more of the same.

(3) Surface activity test 4 g of each paste was dissolved in water to give a volume of 200 ml. The surface tension of the obtained aqueous solution at 25° C. was determined with the use of a surface tension meter (CBVP A-3, mfd. by Kyowa Kagaku Co., Ltd.) and the permeability (this means wetting time) of the same was determined as a permeation period according to Kimura's canvas disc method at 25° C.

As a result, the composition comprising the polyglycerol fatty acid ester alone showed a surface tension of 36.9 dyne/cm and a permeation period longer than 30 minutes. In contrast thereto, those comprising 20% and 40% of the mono acyl glycero phospholipid showed surface tensions of 31.2 dyne/cm and 30.8 dyne/cm, respectively, and permeation periods of 4 minutes and 32 seconds and 3 minutes and 3 seconds, respectively.

(4) Dispersion test on fine inorganic particles 2 g of each paste was dissolved in water to give a volume of 250 ml. 20 ml of the obtained aqueous solution and 1 g of a titanium white pigment were introduced into a Nessler tube and vigorously shaken therein vertically to thereby disperse the pigment in the solution. Then it was allowed to stand in room temperature under observing the dispersion and sedimentation condition. Further 5 ml of a 30% aqueous solution of common salt was added thereto and the mixture was shaken again and allowed to stand under observing the dispersion and sedimentation condition.

The composition comprising the polyglycerol fatty acid ester alone showed aggregation and sedimentation after 20 minutes regardless of the addition of the saline solution. In contrast thereto, the composition comprising 10% of the mono acyl glycero phospholipid to which no saline solution was added showed little sedimentation after one hour, while those comprising 20% or more of the mono acyl glycero phospholipid showed stable dispersion regardless of the addition of the saline solution.

The same procedure was carried out with the use of highly fine grains of calcium carbonate. As a result, the composition comprising the polyglycerol fatty acid ester alone immediately showed aggregation and sedimentation. In the case where the saline solution was added, in particular, the addition of the polyglycerol fatty acid ester accelerated the aggregation and sedimentation compared with a saline solution containing no additive. In contrast thereto, those comprising 20% or more of the mono acyl glycero phospholipid showed stable dispersion after two hours.

EXAMPLE 9

Mono acyl glycero phospholipid B and a polyglycerol fatty acid ester having an HLB of 7 (SY Glyster TS-500 mfd. by Sakamoto Yakuhin Co., Ltd.; mainly comprising stearic acid and having a degree of polymerization of polyglycerol of (6) were mixed together at various weight ratios and each mixture thus obtained was formulated into a 25% by weight aqueous paste.

(1) Emulsification stability test on corn salad oil and aqueous solution of common salt The procedure of Example 8 was follwed. In the case of the composition comprising the polyglycerol fatty acid ester alone, 7% of an oily phase consequently separated out after 3 days. In the case of those comprising 10% of the mono acyl glycero phospholipid 1% of oily phase separated out after 3 days, but in the case of the composition comprising 20% of the mono acyl glycero phospholipid only 2% of oily phases separated out after 2 months. Scarcely any separation was observed in the case of those comprising 30% or more of the same.

EXAMPLE 10

Mono acyl glycero phospholipid B and a polyglycerol fatty acid ester having an HLB of 4 (SY Glyster TS-310 mfd. by Sakamoto Yakuhin Co., Ltd.; mainly comprising stearic acid and having a degree of polymerization of glycerol of (4) were mixed together at various weight ratios and each mixture thus obtained was formulated into a 20% by weight aqueous paste.

(1) Emulsification stability test on corn salad oil and soy sauce

The procedure of Example 8 was following with the use of 2.5 g of each paste. As a result, the emulsion in the case of composition comprising the polyglycerol fatty acid ester alone was completely broken within three days. On the other hand, 10% of an oily phase separated out after seven days in the case of the composition comprising 10% of the mono acyl glycero phospholipid and scarcely any separation was observed after a month in the case of those comprising 20% or more of the same.

EXAMPLE 11

Mono acyl glycero phospholipid E and SY Glyster MS-310 were mixed together at various weight ratios and each mixture thus obtained was formulated into a 20% by weight aqueous paste.

(1) Acid- and salt-resistance test

The procedure of Example 8 was followed with the use of 5 g of each paste to thereby determine the transmittance of each sample at 720 nm.

As a result, in the case of the composition comprising the polyglycerol fatty acid ester alone, the control solution showed a transmittance of 8% while the acidic and saline solutions showed separation of the surfactant. In the case of the composition comprising 32% of the mono acyl glycero phospholipid, the control, acidic and saline solutions showed transmittances of 75%, 62% and 45%, respectively. In the case of that comprising 41% of the same, the control, acidic and saline solutions showed transmittances of 80%, 74% and 67%, respectively. In the case of that comprising 51% of the same, the control, acidic and saline solutions showed transmittances of 86%, 82% and 82%, respectively, i.e., showing little differences.

(2) Surface activity test

The procedure of Example 8 was followed. As a result, the composition comprising the polyglycerol fatty acid ester alone showed a surface tension of 36.9 dyne/cm, and a permeation period was longer than 30 minutes. In contrast thereto, those comprising 15%, 32% and 51% of the mono acyl glycero phospholipids showed surface tensions of 30.8 dyne/cm, 29.4 dyne/cm and 29.5 dyne/cm, respectively, and permeation periods of 8 minutes and 23 seconds, 3 minutes and 48 seconds and 2 minutes and 36 seconds, respectively.

(3) Emulsification stability test on corn salad oil and soy sauce

The procedure of Example 8 was followed. In the case of the composition comprising the polyglycerol fatty acid ester alone, 8% of an oily phase consequently separated out after 30 days. On the other hand, 1% of an oily phase separated out in the case of that comprising 15% of the mono acyl glycero phospholipid while scarcely any separation was observed in the cases of those comprising 23% or more of the same.

(4) Dispersion test on fine inorganic particles

The procedure of Example 8 was followed. As a result, the titanium white pigment showed aggregation and sedimentation after 20 minutes in the case of the composition comprising the polyglycerol fatty acid ester alone regardless of the addition of the saline solution. In contrast thereof, that comprising 15% of the mono acyl glycero phospholipid showed little sedimentation after 3 hours without adding any saline solution and those comprising 23% or more of the same showed stable dispersion after an hour with adding saline solution.

The same test was carried out with the use of highly fine grains of calcium carbonate. In the case of the composition comprising the polyglycerol fatty acid ester alone, aggregation and sedimentation were immediately observed. In the case where the saline solution was added, in particular, the addition of the polyglycerol fatty acid ester accelerated the aggregation and sedimentation compared with a saline solution containing no additive. In the cases of those comprising 15% or more of the mono acyl glycero phospholipid, stable dispersion was observed after two hours. In the cases of those comprising 32% or more of mono acyl glycero phospholipid, stable dispersion was observed after 2 hours even in the presence of the saline solution.

EXAMPLE 12

Mono acyl glycero phospholipid F and SY Glyster TS-500 were mixed together at various weight ratios and each mixture thus obtained was formulated into a 20% by weight aqueous paste.

(1) Emulsification stability test on corn salad oil and soy sauce

The procedure of Example 8 was followed. In the case of the composition comprising the polyglycerol fatty acid ester alone, 7% of an oily phase separated out after 3 days. In the case of that comprising 12% of the mono acyl glycero phospholipid, 1% of an oily phase separated out after one month, while scarcely any separation was observed after two months in the cases of those comprising 19% or more of the same.

EXAMPLE 13

Mono acyl glycero phospholipid A and a sucrose fatty acid ester having an HLB of 15 (Ryoto Sugar Ester S-1670 mfd. by Mitsubishi Kasei Shokuhin Co., Ltd.; mainly comprising stearic acid) were mixed together at various weight ratios and each mixture thus obtained was formulated into an aqueous paste containing 40% by weight of the composition of the present invention.

(1) Acid- and salt-resistance test

To 2.5 g of each paste, water was added to give a volume of 100 ml. To one-part (by volume) portions of the aqueous solution thus formed, one-part (by volume) portions of a 0.2M phthalate buffer solution (ph 3), a 20% aqueous solution of common salt and water were added to respectively give an acidic solution, a saline solution and a control solution and each solution was allowed to stand at room temperature for a day. In the case of the composition comprising the surrose fatty acid ester alone, the acidic and saline solutions immediately showed aggregation and sedimentation. In the cases of those comprising 5 to 20% of the mono acyl glycero phospholipid, milky turbidity slowly proceeded while little turbidity was observed in the cases of those comprising 30% or more of the same. In the case of the composition comprising the sucrose fatty acid esters alone, the control solution showed a transmittance pf 97% at 720 nm after one day while both of the acidic and saline solutions, wherein a precipitate was redispersed prior to the determination, showed a transmittance of 0%. In the case of the composition comprising 30% of the mono acyl glycero phospholipid, the acidic and saline solutions showed transmittances of 70% and 84%, respectively. In the case of that comprising 40% of the same, the acidic and saline solutions showed transmittances of 92% and 97%, respectively. In the case of that comprising 50% of the mono acyl glycero phospholipid, the acidic and saline solutions showed transmittances of 97% and 99%, respectively. In the cases of those comprising 30% or more of the same, each control solution showed a transmittance of 99%.

(2) Emulsification stability test on liquid paraffin and aqueous solution of common salt 1.25 g of each paste containing 0.5 g of the composition of the present invention, 35 ml of liquid paraffin and 65 ml of a 5% aqueous solution of common salt were emulsified with a turbo type homogenizer (AM-8 mfd. by Nippon Seiki Co., Ltd.) at 45° C. and 12,000 rpm for five minutes. The obtained emulsion was introduced into a glass cylinder and stored in an incubator while periodically changing the temperature, i.e., at 20° C. for 12 hours and at 35° C. for 12 hours.

In the case of the composition comprising the sucrose fatty acid ester alone, the separation of 2% by volume, based on the total emulsion system, of an oily phase required on day. On the other hand, in the cases of those comprising 6%, 10%, 20%, 30% and 40% or more of the mono acyl glycero phospholipid, 6, 12, 21, 35 and 45 days were required therefor, respectively. When 0.25 g of the mono acyl glycero phospholipid alone was added to thereby give the same mono acyl glycero phospholipid concentration as that of the case of the composition of the present invention comprising 50% of the mono acyl glycero phospholipid, six days were required therefor, showing that the combined use of the mono acyl glycero phospholipid with the sucrose fatty acid ester improved the effects.

(3) Emulsification stability test on corn salad oil and soy sauce 1.25 g of each paste, 50 g of corn salad oil and 56 g of "koikuchi" soy souce (mfd. by Kikkoman Co., Ltd.) were emulsified in a turbo type homogenizer (AM-8 mfd. by Nippon Seiki co., Ltd.) at 55° C. and 13,000 rpm for six minutes. The emulsion thus formed was introduced into a glass cylinder and stored in an incubator while periodically changing the temperature, i.e., at 20° C. for 12 hours and at 35° C. for 12 hours.

In the case of the composition comprising the sucrose fatty acid ester alone, the separation of 2% of an oily phase required five days and emulsified particles in the emulsified creaming phase aggregated and showed poor redispersbility when shaken. In contrast thereto, in the composition comprising 5% of the mono acyl glycero phospholipid, 14 days were required therefor. In the cases of those comprising 10% or more of the same, 60 or more days were required therefor and the creaming phases showed excellent dispersibility thereafter.

(4) Surface activity test 2.5 g of each paste was dissolved in water to give a volume of 200 ml. The surface tension of the aqueous solution thus obtained was determined at 25° C. with the use of a surface tension meter (CBVP A-3 mfd. by Kyowa Kagaku Co., Ltd.) and the permeability of the same was determined according to Kimura's canvas disc method at 25° C.

As a result, the composition comprising the sucrose fatty acid ester alone showed a surface tension of 34.9 dyne/cm and a permeation period of 7 minutes and 12 seconds. On the other hand, those comprising 5%, 10% and 50% of the mono acyl glycero phospholipid showed surface tensions of 34.6 dyne/cm, 34.3 dyne/cm and 32.6 dyne/cm, respectively, and permeation periods of 5 minutes and 50 seconds, respectively, each showing a successive decrease.

(5) $\beta$-Carotene solubilization test 2.5 g of each paste was dissolved in water to give a volume of 100 ml. With the use of the aqueous solution thus obtained, the procedure of Example 1 was followed and the absorbance of each sample was determined at 455 nm with a spectrometer.

As a result, the composition comprising the sucrose fatty acid ester alone showed an absorbance of 0.102. On the other hand, those comprising 30%, 40% and 50% of the mono acyl glycero phospholipid showed absorbances of 0.309, 0.371 and 0.418, respectively, suggesting that the $\delta$-carotene thus solubilized amounted three to four times as much as that of the former case. 2-ml portions of the centrifuged supernatant were added to 2-ml portions of water, an 8% aqueous solution of common salt and a solution of a pH value of 4 to respectively give a control solution, a saline solution and an acidic solution. As a result, in the case of the composition comprising 30% of the mono acyl glycero phospholipid, both of the acidic and saline solutions showed slight turbidity. On the other hand, the solutions showed stable solubilization in the case of that comprising 50% of the same.

(6) Dispersion test 1.25 g of each paste was dissolved in water to give a volume of 250 ml. 5 ml of the aqueous solution thus obtained and 50 mg of fine particles of β-carotene were introduced into a 15-ml test tube and shaken therein vertically to thereby disperse the particles in the solution. Then the stability of the obtained dispersion and the packing volume of the sedimented grains, which were densely packed and showed primary dispersion to some extent, suggesting that no aggregation occurred, were observed.

Immediately after the shaking, all samples including those comprising no mono acyl glycero phospholipid showed excellent dispersion and a dense precipitate. One day thereafter, the better dispersion and a precipitate of better qualities were observed in a sample comprising a higher amount of the mono acyl glycero phospholipid. To 2-ml portions of each dispersion, 2-ml portions of water, an 8% aqueous solution of common salt and a 0.2 mol phthalatebuffer solution of a pH value of 4 were added to respectively give a control solution, a saline solution and an acidic solution. Thus, in the case of the composition comprising the sucrose fatty acid ester alone, both of the acidic and saline solutions immediately showed sedimentation. In the case of that comprising 30% of the same, the dispersion was significantly stable and that comprising 40% of the same showed a stability comparable to that of the control solution.

EXAMPLE 14

Mono acyl glycero phospholipid C and a sucrose fatty acid ester having an HLB of 14 (Ryoto Sugar Ester P-1570 mfd. by Mitsubishi Kasei Shokuhin Co., Ltd; mainly comprising palmitic acid) were mixed together at variout weight ratios and each mixture thus obtained was formulated into a 20% by weight aqueous paste.

(1) Acid- and salt-resistance test

To 5 g of each paste, water was added to give a volume of 100 ml. With the use of the aqueous solution thus formed, acidic solutions (pH 3 and pH 5) and a 10% aqueous solution of common salt, the procedure of Example 13 was followed. As a result, the composition comprising the sucrose fatty acid ester alone immediately showed milky turbidity, while milky turbidity slowly proceeded in the cases of other samples.

The transmittance determined after one day of the control solution of the composition comprising the sucrose fatty acid ester alone was 96%, while those of the compositions comprising 20% or above of the same were 98%. Both of the acidic and saline solutions of the composition comprising the sucrose fatty acid ester alone showed a transmittance of 0%, when determined after redispersing the precipitate. On the other hand, that of the composition comprising 42% was 64% (pH 5) while those of that comprising 52% of the same were 28% (pH 3), 51% (saline) and 82% (pH 5).

(2) Emulsification stability test on corn salad oil and soy sauce

The procedure of Example 13 was followed with the use of 2.5 g of each paste, 50 g of corn salad oil and 54 g of "koikuchi" soy sauce. The obtained emulsion was introduced into a glass cylinder and stored in an incubator while periodically changing the temperature, i.e., at 20° C. for 12 hours and at 35° C. for 12 hours.

In the case of the composition comprising the sucrose fatty acid ester alone, the separation fo 2% of an oily phase required 6 days. On the other hand, a month or longer was required therefor in the cases of those comprising 15% or more of the mono acyl glycero phospholipid, while little separation was observed in the cases of those comprising 30% or more of the same.

EXAMPLE 15

Mono acyl glycero phospholipid A and a sucrose fatty acid ester having an HLB of 11 (Ryoto Sugar Ester S-1170 mfd. by Mitsubishi Kasei Shokuhin Co., Ltd.; Mainly comprising stearic acid) were fixed together at various weight ratios and each mixture thus obtained was formulated into a 20% by weight aqueous paste.

(1) Acid- and salt-resistance test

The procedure of Example 14 was followed with the use of acidic solutions of pH 3 and pH 5 and a 10% aqueous solution of common salt. As a result, only the composition comprising the sucrose fatty acid ester alone immediately showed mikly turbidity. The transmittance at 720 nm determined after one day of the control solution of the composition comprising the sucrose fatty acid ester alone was 57%. The control solution of the composition comprising 20% of the mono acyl glycero phospholipid showed a transmittance of 90%, while those comprising 40% or more of the same showed 99% thereof. Both of the acidic and saline solutions of the composition comprising the sucrose fatty acid ester alone showed a transmittance of neary 0%. In contrast thereto, that comprising 30% of the mono acyl glycero phospholipid showed a transmittance of 62% (pH 5), that comprising 40% of the same showed transmittances of 32% (saline) and 91% (pH 5), that comprising 50% of the same showed transmittances of 52% (pH 3), 83% (saline) and 94% (pH 5) and that comprising 60% of the same showed transmittances of 88% (pH 3), 99% (saline) and 96% (pH 5).

(2) Emulsification stability test on corn salad oil and soy sauce

Similar to Example 14, an emulsion of each paste, corn salad oil and "koikuchi" soy sauce was introduced into a glass cylinder and stored in an incubator while periodically changing the temperature, i.e., at 20° C. for 12 hours and at 35° C. for 12 hours. In the case of the composition comprising the sucrose fatty acid ester alone, a creaming phase aggregated accompanied by the loss of flowability and 25% of an oily phase separated out after a month. On the other hand, 2% of an oily phase separated out in the case of that comprising 10% of the mono acyl glycero phospholipid while little separation was observed after a month in the cases of those comprising 20% or more of the same.

EXAMPLE 16

Mono acyl glycero phospholipid C and Ryoto Sugar Ester S-1170 were mixed together at various weight ratios and each mixture thus obtained was formulated into a 20% by weight aqueous paste.

(1) Acid- and salt-resistance test

The procedure of Example 14 was followed with the use of an acidic solution (pH 5) and a 10% aqueous solution of common salt. The control solutions of the compositions comprising 24% and 37% or more of the mono acyl glycero phospholipid showed transmittances at 720 nm of 88% and 91%, respectively, after a day. The acidic and saline solutions of the composition comprising 52% of the same showed transmittances of 60% and 35%, respectively.

(2) Emulsification stability test on corn salad oil and soy sauce

Similar to Example 14, an emulsion of each paste, corn salad oil and "koikuchi" soy sauce was introduced into a glass cylinder and stored in an incubator while periodically changing the temperature, i.e., at 20° C. for 12 hours and at 35° C. for 12 hours.

In the case of the composition comprising 11% of the mono acyl glycero phospholipid, 1% of an oily phase separated out after a month. In contrast thereto, little separation was observed in the cases of those comprising 24% or more of the same.

EXAMPLE 17

Mono acyl glycero phospholipid D and Ryoto Sugar Ester S-1670 were mixed together at various weight ratios and each mixture thus obtained was formulated into a 25% by weight aqueous paste.

(1) Emulsification stability test on corn salad oil and soy sauce

The procedure of Example 13 was followed wholly except that 2 g of each paste was used. The emulsion of the paste, corn salad oil and "koikuchi" soy sauce thus obtained was introduced into a glass cylinder and stored in an incubator while periodically changing the temperature, i.e., at 20° C. for 12 hours and at 35° C. for 12 hours.

As a result, scarcely any separation of any oily phase was observed after one month.

(2) Surface activity test 10 g of each paste was dissolved in water to give a volume of 500 ml. The surface tension and permeability of the obtained aqueous solution at 25° C. were determined each in the same manner as the one described in Example 13.

The composition comprising the sucrose fatty acid ester alone showed a surface thension of 34.6 dyne/cm and a permeation period of 7 minutes and 12 seconds. In contrast thereto, those comprising 6%, 12% and 29% of the same showed surface tensions of 34.4 dyne/cm, 34.0 dyne/cm and 31.1 dyne/cm, respectively, and permeation periods of 4 minutes and 42 seconds, 3 minutes and 24 seconds and 2 minutes and 15 seconds, respectively.

(3) Emulsificaiton stability test on grapefruit juice and corn salad oil 1 g of each paste was dissolved in water to give a volume of 50 ml. 50 ml of the aqueous solution thus obtained, 50 ml of resonstituted grapefruit juice (pH 3.31) and 25 ml of corn salad oil were mixed and the mixture was emulsified and stored in an incubator at 40° C. in the same manner as the one described in regard to emulsification stability test on corn salad oil and soy sauce in Example 13, to thereby observe the stability of the emulsion with the elapse of time.

In the case of the composition comprising the sucrose fatty acid ester alone, a creaming phase aggregated accompanied by the loss of the flowability and separation of an oily phase began after six days. In contrast thereto, no separation was observed after 21 days and a creaming phase was highly flowable and readily dispersed again, in the case of the composition comprising 10% of the mono acyl glycero phospholipid.

(4) $\beta$-Carotene solubilizaiton test 1 g of each paste was dissolved in water to give a volume of 25 ml. The absorbance of the aqueous solution thus obtained was determined at 455 nm with a spectrometer, similar to Example 13.

As a result, the composition comprising the sucrose fatty acid ester alone showed an absorbance of 0.102, while those comprising 18%, 30% and 39% of the mono acyl glycero phospholipid showed absorbances of 0.154, 0.181 and 0.256, respectively, showing an increase in the amount of the solubilized $\beta$-carotene. In the case of the composition comprising 30% of the mono acyl glycero phospholipid, the saline and acidic solutions showed somewhat milky turbidity. On the other hand, that comprising 39% of the same showed stable solubilization.

(5) Dispersion test on fine inorganic particles 1 g of each paste was dissolved in water to give a volume of 125 ml. 20 ml of the aqueous solution thus obtained and 1 g of a titanium white pigment were introduced into a Nessler tube and vigorously shaken therein vertically to thereby disperse the pigment in the solution. After adding 5 ml of a 30% aqueous solution of common salt, the mixture was shaken again and allowed to stand at room temperature under observing the dispersion and sedimentation condition.

As a result, the composition comprising the sucrose fatty acid ester alone immediately showed aggregation and sedimentation. In contrast thereto, those comprising 12% or more of the same showed stable dispersion after three hours.

EXAMPLE 18

Mone acyl glycero phospholipid F and Ryoto Sugar Ester S-1670 were mixed together at various weight ratios and each mixture thus obtained was formulated into a 25% by weight aqueous paste.

(1) Emulsification stability test on corn salad oil and soy sauce

Similar to Example 17, an emulsion comprising each paste, corn salad oil and "koikuchi" soy sauce was introduced into a glass cylinder and stored in an incubator while periodically changing the temperature, i.e., at 20° C. for 12 hours and at 35° C. for 12 hours.

As a result, scarcely any separation of an oily phase was observed after one month.

(2) Emulsification stability test on Grapefruit juice and corn salad oil

Similar to Example 17, 50 ml of a 0.5% aqueous solution, 50 ml of grapefruit juice (pH 3.31) and 50 ml of corn salad oil were mixed together. Then the obtained mixture was emulsified at 60° C. in the same manner as the one described in Example 13 and stored at 40° C. to thereby observe the stability thereof with the elapse of time.

In the case of the composition comprising the sucrose fatty acid ester alone, a creaming phase aggregated and lost the flowability and separation of an oily phase began after six days. In contrast thereto, in the case of the composition comprising 10% of the mono acyl glycero phospholipid, no separation of any oily phase was observed after 21 days and a creaming phase was highly flowable and readily dispersed.

EXAMPLE 19

Mono acyl glycero phospholipid D and Ryoto Sugar Ester S-1170 were mixed together at various weight ratios and each mixture thus obtained was formulated into a 20% by weight aqueous paste.

(1) Emulsification stability test on corn salad oil and soy sauce

Similar to Example 14, an emulsion comprising each paste, corn salad oil and "koikuchi" soy sauce was introduced into a glass cylinder and stored in an incubator while perodically changing the temperature, i.e., at 20° C. for 12 hours and at 35° C. for 12 hours.

As a result, in the case of the composition comprising 12% of the mono acyl glycero phospholipid, 1% of an oily phase separated out after one month. On the other hand, those comprising 18% or more of the same showed scarcely any separation.

(2) Surface activity test 5 g of each paste was dissolved in water to give a volume of 200 ml. The surface tension and permeability of the aqueous solution thus obtained were determined at 25° C. each in the same manner as the one described in Example 13.

As a result, the composition comprising the sucrose fatty acid ester alone showed a surface tension of 34.9 dyne/cm and a permeation period of 26 minutes and 42 seconds. In contrast thereto, those comprising 12%, 20% and 29% of the same showed surface tensions of 32.1 dyne/cm, 31.4 dyne/cm and 31.0 dyne/cm, respectively, and permeation periods of 4 minutes and 36 seconds, 3 minutes and 54 seconds and 3 minutes and 36 seconds, respectively.

(3) Emulsification stability test on juice and corn salad oil 1 g of each paste was dissloved in water to give a volume of 40 ml. With the use of the aqueous solution thus obtained, grapefruit juice and corn salad oil were emulsified in the same manner as the one described in Example 17. The resulting emulsion was stored at 40° C. and the stability of the same was observed with the elaspe of time.

As a result, in the case of the composition comprising the sucrose fatty acid ester alone, a creaming phase aggregated and lost the flowability and an oily phase began to separate on the third day and amounted to 6% after 21 days. In contrast thereto, those comprising 10% or more of the mono acyl glycero phospholipid showed no separation after 21 days and creaming phases thereof were highly flowable and readily redispersed.

EXAMPLE 20

Mono acyl glycero phospholipid G and Ryoto Sugar Ester S-1670 were mixed together at various weight ratios and each mixture thus obtained was formulated into a 20% by weight aqueous paste.

(1) Emulsification stability test on corn salad oil and soy sauce

Similar to Example 14, an emulsion comprising each paste, corn salad oil and "Koikuchi" soy sauce was introduced into a glass cylinder and stored in an incubator while periodically changing the temperature, i.e., at 20° C. for 12 hours and at 35° C. for 12 hours.

As a result, 1% of an oily phase separated out after one month in the case of the composition comprising 5% of the mono acyl glycero phospholipid, while scarcely any separation was observed in the cases of those comprising 10% or more of the same.

EXAMPLE 21

Six parts by weight of Ryoto Sugar Ester S-1170 and four parts by weight of mono acyl glycero phospholipid D were dissolved in 90 parts by weight of ethanol.

50 g of the solution thus obtained was mixed with 500 g of a alkali treated cocoa powder, which contained 23% of fat in a Kenwood mixer under stirring. Then the resulting mixture was dried in vacuo and ground to give an instant cocoa product.

2 g of this instant cocoa was suspended on 100 ml of water. The whole powder required 3 minutes and 42 seconds for sedimentation. In the case of a comparative cocoa powder prepared with the use of the sucrose fatty acid ester alone, 17 minutes and 36 seconds was required therefor.

EXAMPLE 22

Mono acyl glycero phospholipid B and a sucrose fatty acid ester having an HLB of 7 (Ryoto Sugar Ester S-770 mfd. by Mitsubishi Kasei Shokuhin Co., Ltd.; mainly comprising stearic acid) were mixed together at various weight ratios and each mixture thus obtained was formulated into a 20% by weight aqueous paste.

(1) Acid- and salt-resistance test 2.5 g of each paste was added to water to give a volume of 100 ml. To one-part (by volume) portions of the aqueous solution thus obtained, one-part (by volume) portions of a 0.2M phthalate buffer solution (pH 3), a 20% aqueous solution of common salt and water were added to give an acidic solution, a saline solution and a control solution, respectively. Each solution thus formed was heated to 60° C. for ten minutes and allowed to cool at room temperature.

As a result, in the case of the composition comprising the sucrose fatty acid ester alone, the acidic and saline solutions immediately showed aggregation and precipitation. In the cases of those comprising 10 to 60% of the mono acyl glycero phospholipid, milky turbidity proceeded slowly, while little turbidity was observed in the cases of those comprising 70% or more of the same. In the case of the composition comprising the sucrose fatty acid ester alone, the control solution showed a transmittance of 42% at 720 nm after one day, while both of the acidic and saline solutions, wherein formed precipitate was redispersed prior to the determination, showed a transmittance of 0%. In the case of the composition comprising 40% of the mono acyl glycero phospholipid, the control and saline solutions showed transmittance of 96% and 59%, respectively. In the case of that comprising 60% of the same, the control, acidic and saline solutions showed transmittance of 99%, 51% and 94%, respectively.

(2) Emulsification stability test on liquid paraffin and aqueous solution of common salt 2.5 g of each paste, 35 ml of liquid paraffin and 65 ml of a 5% aqueous solution of common salt were emulsified in a turbo type homogenizer (AM-8 mfd. by Nippon Seiki Co., Ltd.) at 45° C. and 12,000 rpm for five minutes. The emulsion thus formed was introduced into a glass cylinder and stored in an incubator while periodically changing the temperature, i.e., at 20° C. for 12 hours and at 35° C. for 12 hours.

As a result, the separation of 2% by volume, based on the total emulsion system, of an oily phase required one day in the case of the composition comprising the sucrose fatty acid ester alone. On the other hand, in the case of those comprising 10%, 20%, 30% and 50% of the mono acyl glycero phospholipid, 10 days, 17 days, 28 days and 42 days were required therefor, respectively. When 0.25 g of the mono acyl glycero phospholipid alone was added, i.e., giving the same concentration of the mono acyl glycero phospholipid in the composition of the present invention comprising 50% of the mono acyl glycero phospholipid, six days were required therefor, showing that the combined use of the mono acyl glycero phospholipid with the sucrose fatty acid ester improved the effects.

(3) Emulsification stability test on corn salad oil and soy sauce 2.5 g of each paste, 50 g of corn salad oil and 56 g of "Koikuchi" soy sauch were emulsified in a turbo type homogenizer (AM-8 mfd. by Nippon Seiki Co., Ltd.) at 55° C. and 13,000 rpm for six minutes. The emulsion thus obtained was introduced into a glass cylinder and stored in an incubator while periodically changing the temperature, i.e., 20° C. for eight hours and 40° C. for 16 hours.

As a result, in the case of the composition comprising the sucrose fatty acid ester alone, the separation of 2% of an oily phase required four days, the emulsified particles in a creaming phase aggregated and showed poor redispersibility by shaking and the emulsion was broken after 21 days. In contrast thereto, those comprising 10% and 20% or more of the mono acyl glycero phospholipid required 14 days and 60 days or longer therefor, respectively. The creaming phases showed excellent redispersibility thereafter in the latter cases.

(4) Surface acitivity test 5 g of each paste was dissloved in water to give a volume of 200 ml. The surface tension of the aqueous solution thus obtained was determined at 25° C. with the use of a surface tension meter (CBVP A-3 mfd. by Kyowa Kagaku Co., Ltd.) while the permeability thereof was determined as a permeation period at 25° C. according to Kimura's canvas disc method.

As a result, the composition comprising the sucrose fatty acid ester alone showed a surface tension of 34.8 dyne/cm and a permeation period longer than 30 minutes. In contrast thereto, those comprising 20% and 40% of the mono acyl glycero phospholipid showed surface tensions of 31.6 dyne/cm and 30.9 dyne/cm, respectively, and permeation periods of 6 minutes and 48 seconds and 4 minutes and 59 seconds, respectively.

EXAMPLE 23

An emulsification stability test on corn salad oil and soy sauce was carried out in the same manner as the one described in Example 22, with the use of a 20% by weight aqueous paste of a composition comprising 30 parts by weight of mono acyl glycero phospholipid B and 70 parts by weight of a sucrose fatty acid ester having an HLB of 9 (Ryoto Sugar Ester S-970 mfd. by Mitsubishi Kasei Shokuhin Co., Ltd.; mainly comprising stearic acid).

As a result, the separation of 2% of an oily phase required seven days in the case of the composition comprising the sucrose fatty acid ester alone. The emulsified particles in a creaming phase aggregated and showed no redispersibility by shaking and the emulsion was broken after 21 days in this case. In contrast thereto, in the cases of those comprising the mono acyl glycero phospholipid, no separation was observed after 60 days and creaming phases showed excellent redispersibility.

The same procedure was repeated except that the soy sauce was replaced by reconstituted orange juice (pH 3.5).

As a result, the separation of 2% of an oily phase required 35 days in the case of the composition comprising the sucrose fatty acid ester alone. On the other hand, no separation was observed after 60 days and creaming phases showed excellent redispersibility in the cases of those comprising the mono acyl glycero phospholipid.

EXAMPLE 24

An emulsification stability test on corn salad oil and soy sause was carried out in the same manner as the one described in Example 22 with the use of a 20% by weight aqueous paste of a composition comprising 30 parts by weight of mono acyl glycero phospholipid B and 70 parts by weight of a sucrose fatty acid ester having an HLB of 5 (Ryoto Sugar Ester S-570 mfd. by Mitsubishi Kasei Shokuhin Co., Ltd.; mainly comprising stearic acid). As a result, in the case of the composition comprising the sucrose fatty acid ester alone, 2% of an oily phase separated out after four days and the emulsion was broken after 15 days. In contrast thereto, in the cases of those comprising the mono acyl glycero phospholipid, only 1% of an oily phase separated out after 60 days.

The same procedure was repeated except that the soy sauce was replaced with reconstituted orange juice (pH 3.5). As a result, in the case of the composition comprising the sucrose fatty acid ester alone, 2% of an oily phase separated out after eight days and the emulsion was broken after 21 days. In contrast thereto, those comprising the mono acyl glycero phospholipid showed no separation after 60 days.

EXAMPLE 25

Mono acyl glycero phospholipid E and a sucrose fatty acid ester having an HLB of 5 (Ryoto Sugar Ester S-570 mfd. by Mitsubishi Kasei Shokuhin Co., Ltd.; mainly comprising stearic acid) were mixed together at various weight ratios and each mixture thus obtained was formulated into a 20% by weight aqueous paste.

With the use of these paste, an emulsification stability test on corn salad oil and soy sauce was carried out in the same manner as the one described in Example 22.

As a result, the composition comprising 11% by weight of the mono acyl glycero phospholipid was inferior to that comprising 15% by weight of the same in the redispersibility and homogeneity fo the creaming phase, although little separation was observed in both cases. As a matter of course, scarcely any separation was observed in the cases of those comprising 15% by weight or more of the same.

EXAMPLE 26

Mono acyl glycero phospholipid E and Ryoto Sugar Ester S-770 were mixed together at various weight ratios and each mixture thus obtained was formulated into a 20% by weight aqueous paste.

60 g of each paste, 600 g of rapeseed oil and 400 g of "Koikuchi" soy sauce were stirred vigorously under heating to thereby pre-emulsify the mixture. Then the mixture was homogenized with a homogenizer (15 M-8 BA mfd. by Manton Gaulin Manufacturing Co.) by applying pressures of 300 Kg/cm$^2$ and 20 Kg/cm$^2$ at the first and second valves, respectively, at 40° C. twice to thereby give an emulsion. The obtained emulsion was allowed to stand at 40° C. for 60 days under observing the emulsification stability of the same.

In the case of the composition comprising the sucrose fatty acid ester alone, 5% of an oily phase separated out after two days. On the other hand, only a trace amount of an oily component separated out in the case of composition comprising 11% of the mono acyl glycero phospholipid. In the case of those comprising 23% and 41% of the same, no oily phase separated out and creaming-up proceeded slowly, showing excellent redispersibility.

5 g of each paste was dissolved in water to give a volume of 200 ml. The surface tension and permeability of the aqueous solution thus obtained were determined at 25° C. each in the same manner as the one described in Example 22.

The composition comprising the sucrose fatty acid ester alone showed a surface tension of 34.8 dyne/cm and a permeation period longer than 30 minutes. In contrast thereto, those comprising 15%, 31.5% and 51% of the mono acyl glycero phospholipid showed surface tensions of 31.5 dyne/cm, 29.6 dyne/cm and 29.8 dyne/cm, respectively, and permeation periods of 9 minutes and 53 seconds, 4 minutes and 25 seconds and 2 minutes and 23 seconds, respectively, showing improved surface activities.

1 g of each paste was dissloved in water to give a volume of 100 ml. 20 ml of the aqueous solution thus obtained and 1 g of a titanium white pigment or highly fine grains of calcium carbonate were introduced into a Nessler tube and vigorously shaken therein vertically to thereby disperse the particles in the solution. After adding 5 ml of a 30% aqueous solution of common salt, the mixture was shaken again and allowed to stand at room temperature under observing the dispersion and sedimentation condition.

In the case of the composition comprising the sucrose fatty acid ester alone, both of the dispersions immediately showed aggregation and sedimentation. On the other hand, in the cases of those comprising 23% or more of the mono acyl glycero phospholipid, each dispersion was stable even after three hours.

EXAMPLE 27

Mono acyl glycero phospholipid F and Ryoto Sugar Ester S-970 were mixed together at various weight ratios and each mixture thus obtained was formulated into a 20% by weight aqueous paste.

With the use of these paste, an emulsification stability test on corn salad oil and soy sauce was carried out in the same manner as the one described in Example 22.

In the case of the composition comprising the sucrose fatty acid ester alone, the separation of 2% of an oily phase required seven days and the emulsion was broken after 21 days. In contrast thereto, those comprising 12% or more of the mono acyl glycero phospholipid, oily phase scarcely separated out after 60 days. Those comprising 19% or more of the same showed excellent redispersibility.

EXAMPLE 28

Mono acyl glycero phospholipid B and sorbitan monostearate (Emasol S 10-F mfd. by Kao Co., Ltd.) were mixed together at various weight ratios and each mixture thus obtained was formulated into a 20% by weight aqueous paste.

(1) Acid- and salt-resistance test

To 1 g of each paste, water was added to give a volume of 100 ml. To one-part (by volume) portions of the aqueous solution thus obtained, one-part (by volume) portion of a 0.2M phthalate buffer solution (pH 3), a 20% aqueous solution of common salt and water were added to give an acidic solution, a saline solution and a control solution, respectively. These solutions were heated to 60° C. for ten minutes and allowed to cool indoor.

In the case of the composition comprising the sorbitan fatty acid ester alone, the dispersions in water thus formed immediately showed aggregation and precipitation under the acidic condition or in the presence of the salt. In the cases of the compositions comprising 10 to 30% of the mono acyl glycero phospholipid, milky turbidity proceeded slowly while little increase in the turbidity was observed, i.e., showing almost the same transmittance as those of the controls, in the cases of those comprising 40% or more of the same. The transmittance at 720 nm of the control dispersion of the composition comprising the sorbitan fatty acid ester alone determined immediately after the preparation was 0.4% and a precipitate was observed therein after allowing it to stand for one day. The transmittances of the control, acidic and saline solutions of the composition comprising 40% of the mono acyl glycero phospholipid determined after one day were 44%, 40% and 29%, respectively. On the other hand, those of the control, acidic and saline solutions of the composition comprising 50% of the same were 62%, 62% and 63%, respectively.

(2) Emulsification stability test on corn salad oil and soy sauce 2.5 g of each paste, 50 g of corn salad oil and 56 g of "Koikuchi" soy sauce were emulsified in a turbo type homogenizer (AM-8 mfd. by Nippon Seiki Co., Ltd.) at 55° C. and 13,000 rpm for six minutes. The emulsion thus formed was introduced into a glass cylinder and stored in an incubator while periodically changing the temperature, i.e., at 20° C. for eight hours and at 40° C. for 16 hours.

As a result, most of the oily component separated out after two days in the case of the composition comprising the sorbitan fatty acid ester alone. In contrast thereto, only 5% and 3% of an oily phases separated out after seven days and two months, respectively, in the cases of those comprising 10% and 20% of the mono acyl glycero phospholipid. Those comprising 30% or more of the same showed scarcely any separation.

(3) Surface activity test 5 g of each paste was dissloved in water to give a volume of 200 ml. The surface tension of the aqueous solution thus obtained was determined at 25° C. with a surface tension meter (CBVP A-3 mfd. by Kyowa Kagaku Co., Ltd.) while the permeability of the same was determined at 25° C. as a permeation period according to Kimura's canvas disc method.

As a result, the composition comprising the sorbitan fatty acid ester alone showed a surface tension of 46.4 dyne/cm and a permeation period longer than one hour. On the other hand, those comprising 30% and 50% of the mono acyl glycero phospholipid showed surface tension of 31.9 dyne/cm and 30.8 dyne/cm, respectively, and permeation periods of 6 minutes and 3 seconds and 3 minutes and 16 seconds, respectively.

The permeation period of a sucrose fatty acid ester (Ryoto Sugar Ester S-1670), which has the highest permeability among all nonionic surfactants approved as food additives in Japan, was 7 to 8 minutes.

EXAMPLE 29

With the use of mono acyl glycero phospholipid B and sorbitan monooleate (Span-80 mfd. by Kao Co., Ltd.), mixtures of the sorbitan fatty acid ester and mono acyl phospholipid at ratios of 80/20 and 60/40 were prepared and each mixture was formulated into a 20% by weight aqueous paste. An emulsification stability test on corn salad oil and soy sauce was carried out with the use of these pastes in the same manner as the one described in Example 28.

In the case of the composition comprising the sorbitan fatty acid ester alone, the emulsion was immediately broken. On the other hand, in the case of the composition comprising 20% of the mono acyl glycero phospholipid, 2% and 5% of an oily phase separated out after one month and two months, respectively. In the case of that comprising 40% of the same, only 2% of an oily phase separated out after two months.

The same procedure was repeated except that the soy sauce was replaced by reconstituted orange juice. As a result, 2% and 30% of an oily phase separated out after five days and one month, respectively, in the case of the composition comprising the sorbitan fatty acid ester alone. In contrast thereto, scarcely any separation was observed in the cases of those comprising 20% or more of the mono acyl glycero phospholipid after two months.

EXAMPLE 30

Mono acyl glycero phospholipid D and Ermasal S-10-F were mixed together at various weight ratios and each mixture thus obtained was formulated into a 20% by weight aqueous paste.

(1) Acid- and salt-resistance test

The procedure of Example 28 was followed. As a result, the control solution of the composition comprising the sorbitan fatty acid ester alone showed a transmittance of 0.4% at 720 nm after one day. When allowed to stand, the solution showed precipitation. The control and acidic solutions of the composition comprising 22% of the mono acyl glycero phospholipid showed transmittances of 21% and 13%, respectively. The control, acidic and saline solutions of that comprising 39% of the same showed transmittances of 42%, 32% and 15%, respectively. The control, acidic and saline solutions of that comprising 49% of the same showed transmittances of 62%, 61% and 62%, respectively.

(2) Emulsification stability test on corn salad oil and soy sauce

The procedure of Example 28 was followed. As a result, most of the oily component separated out after two days in the case of the composition comprising the sorbitan fatty acid ester alne. On the other hand, scarcely any separation was observed in the case of the composition comprising 14% of the mono acyl glycero phospholipid. In this case, emulsified particles aggregated within a creaming phase and the redispersibility was somewhat poor. However those comprising 22% or more of the same showed scarcely any separation and stable emulsification.

(3) Emulsification stability test on corn salad oil and orange juice

The procedure of Example 29 was followed. As a result, scarcely any separation of an oily phase was observed after two months in the cases of the compositions comprising 14% or more of the mono acyl glycero phospholipid, although those containing approximately 22% of the mono acyl glycero phospholipid showed somewhat poor redispersibility of creaming phases. However those comprising 30% or more of the mono acyl glycero phospholipid showed excellent redispersibility.

(4) Dispersion test on fine inorganic particles 2 g of each was dissloved in water to give a volume of 200 ml. 20 ml of the aqueous solution thus obtained and 1 g of a titanium white pigment were introduced into a Nessler tube and vigorously shaken therein vertically to thereby disperse the pigment in the solution. Then it was allowed to stand in room temperature under observing the dispersion and sedimentation condition.

The composition comprising the sorbitan fatty acid ester alone showed aggregation and sedimentation after 20 minutes. In contrast thereto, that comprising 22% of the mono acyl glycero phospholipid showed scarcely any sedimentation and stable dispersion after one hour.

EXAMPLE 31

Mono acyl glycero phospholipid B and a glycerol fatty acid monoester containing 97% of the monoester (Emulsy MS mfd. by Riken Vitamin Co., Ltd.; mainly comprising stearic acid) were mixed together at various weight ratios and each mixture thus obtained was formulated into a 20% by weight aqueous paste.

(1) Acid- and salt-resistance test

Water was added to each paste to give a 1% aqueous solution. To one-part (by volume) portions of the obtained aqueous solution, one-part (by volume) portions of a 0.2M phthalate buffer solution (pH 3), a 20% aqueous solution of common salt and water were added to give an acidic solution, a saline solution and a control solution, respectively. Each solution was heated to 60° C. for ten minutes and then allowed to cool in room temperature. In the case of the composition comprising the glycerol fatty acid monoester, no dispersion in water was observed, because it was insoluble or nondispersible in water. On the other hand, in the cases of those comprising 10 to 30% of the mono acyl glycero phospholipid, milky turbidity proceeded slowly. Those comprising 40% or more of the same showed little or substantially no turbidity. After cooling, the control, acidic and saline solutions of the composition comprising 40% of the mono acyl glycero phospholipid showed transmittances at 720 nm of 96%, 59% and 91%, respectively, while the control, acidic and saline solutions of that comprising 50% of the same showed transmittances at 720 nm of 98%, 97% and 99%, respectively.

(2) Emulsification stability test on liquid paraffin and aqueous solution of common salt 2.5 g of each paste, 35 ml of liquid paraffin and 70 ml of a 5% aqueous solution of common salt were emulsified in a turbo type homogenizer (AM-8 mfd. by Nippon Seiki Co., Ltd.) at 45° C. and 12,000 rpm for five minutes to give a oil-in-water emulsion. This emulsion was introduced into a glass cylinder and stored in an incubator while periodically changing the temperature, i.e., 20° C. for 12 hours and 35° C. for 12 hours.

In the case of the composition comprising the glycerol fatty acid monoester alone, emulsification was impossible and an oily phase immediately separated out.

In the case of the composition comprising 20% of the mono acyl glycero phospholipid, four days were required for the separation of 2% by volume of an oily phase. In this case, the oily phase could be redispersed by shaking after creaming. In the case of the composition comprising 10% of the mono acyl glycero phospholipid, 4% of an oily phase separated out after one day, although it could be redispersed by shaking. Separately, 0.15 g and 0.05 g of the mono acyl glycero phospholipid alone, i.e., giving the same concentrations of the mono acyl glycero phospholipid as those comprising 30% and 10% of the mono acyl glycero phospholipid, were added. Thus 22% of an oily phase separated out after 20 days in the former (0.15 g) case, while 13% of an oily phase separated out after one day in the latter (0.05 g) case, showing that the combined use of the mono acyl glycero phospholipid with the glycero fatty acid monoester improved the effects.

(3) Emulsification stability test on corn salad oil and soy sauce 2.5 g of each paste, 50 g of corn salad oil and 56 g of "Koikuchi" soy sauce were emulsified together in a turbo type homogenizer (AM-8 mfd. by Nippon Seiki Co., Ltd.) at 55° C. and 13,000 rpm for six minutes. The obtained emulsion was introduced into a glass cylinder and stored in an incubator while periodically changing the temperature, i.e., at 20° C. for 12 hours and at 35° C. for 12 hours.

As a result, an oily phase immediately separated out and emulsification was impossible in the case of the composition comprising the glycerol fatty acid monoester alone.

The composition comprising 20%, 30% and 50% or more of the mono acyl glycero phospholipid showed emulsification stabilities, as expressed by the amounts of separated oily phases after 30 days, of 7%, 2% and nearly 0%, respectively.

(4) Surface activity test

To each paste, water was added to give an aqueous solution of 0.5% in concentration. The surface tension of the obtained aqueous solution was determined at 25° C. with a surface tension meter (CBVP A-3 mfd. by Kyowa Kagaku Co., Ltd.) and the permeability thereof was determined according to Kimura's canvas disc method at 25° C. FIG. 1 shows the results wherein—O—O—represents the permeation period while—X—X—represents the surface tension.

In the case of the composition comprising the glycerol fatty acid monoester alone, each determination was impossible since it was insoluble in water.

FIG. 1 obviously shows that the combined use of the mono acyl glycero phospholipid and the glycerol fatty acid monoester whould exhibit synergistic effects.

(5) β-Carotene solubilization test 5 g of each paste was dissloved in water to give a volume of 100 ml. 10 ml of the aqueous solution thus obtained and 10 mg of powdery β-carotene were introduced into a 30-ml test tube and shaken therein at 30° C. for 42 hours to thereby solubilize the β-carotene. The solubilized matter was then centrifuged at 3000 rpm. To 2 ml of the obtained supernatant. 8 ml of a mixture of chloroform and ethanol (1:4) was added and the absorbance of the resulting mixture was determined at 455 nm with a spectrometer.

The composition comprising the mono acyl glycero phospholipid alone showed an absorbance of 0.581 while those comprising 85% and 70% of the mono acyl glycero phospholipid showed absorbances of 0.543 and 0.411, respectively.

(6) Dispersion test on fine inorganic particles 1 g of each paste was dissloved in water to give a volume of 100 ml. 20 ml of the aqueous solution thus obtained and 1 g of a titanium white pigment were introduced into a Nessler tube and vigorously shaken therein vertically to thereby disperse the pigment in the solution. Then the dispersion was allowed to stand under observing the sedimentation condition. 5 ml of a 30% aqueous solution of common salt was further added thereto and the mixture was shaken again and allowed to stand in room temperature under observing the dispersion and sedimentation condition.

As a result, in the case of the composition comprising the mono acyl glycero phospholipid alone, aggregation and sedimentation were immediately observed regardless of the addition of the saline solution. In contrast thereto, those comprising 10 to 20% of the mono acyl glycero phospholipid showed sedimentation after one hour when the saline solution was added. However no sedimentation was observed in those cases wherein no saline solution was added. Those comprising 90%, 75% and 30% of the mono acyl glycero phospholipid showed no sedimentation regardless of the addition of the saline solution.

The same test was carried out with the use of highly fine grains of calcium carbonate. As a result, the composition comprising the mono acyl glycero phospholipid alone rather accelerated the aggregation and precipitation. However those comprising 30 to 70% of the same showed stable dispersion regardless of the addition of the saline solution.

EXAMPLE 32

Mono acyl glycero phospholipid H and Emulsy MS at various weight ratios were dissloved in ethanol and the ethanol was distilled off in vacuo to thereby give solid products. Each solid product thus obtained was ground to give a composition in the form of grains.

(1) Oil solubility test 2 g of each composition was dissloved in liquid paraffin (Carnation Oil mfd. by Witco Chemical Corp.) under heating and stirring.

As a result, the composition comprising the mono acyl glycero phospholipid alone was completely insoluble therein. On the other hand, those comprising the glycerol fatty acid ester and mono acyl phospholipid at a ratio exceeding 30/70 (glycerol fatty acid monoester and mono acyl glycero phospholipid at a ratio exceeding 39/61) were highly soluble therein. In the cases of those each comprising the glycerol fatty acid ester in a lower amount than the one as defined above, the solubility would increase with an increase in the content of the glycerol fatty acid ester.

A comparative solubilization test was carried out with the use of a composition comprising 10% of polyglycerol fatty acid ester having an HLB of 15 (Sun Soft G-17-U) and 90% of glycerol fatty acid monoester. However the comparative composition was insoluble therein.

(2) Surface activity test

The surface tensiodn and permeability of each composition were determined each in the same manner as the one described in Example 31. In the case of the composition comprising the glycerol fatty acid ester alone, each determination was impossible since it was insoluble in water.

As a result, the composition comprising the mono acyl glycero phospholipid alone showed a surface tension of 30.9 dyne/cm and a permeation period of 58 seconds. On the other hand, those comprising the glycerol fatty acid ester and phosphatide at ratios of 15/85, 30/70 and 45/55 showed surface tensions of 30.6 dyne/cm, 30.7 dyne/cm and 30.3 dyne/cm, respectively, and permeation periods of 63 seconds, 99 seconds and 185 seconds, respectively. The composition comprising these materials at ratio of 70/30 showed a surface tension of 28.5 dyne/cm.

(3) Emulsification stability test on corn salad oil and soy sauce 0.5 g of each composition comprising 50% or more of the mono acyl glycero phospholipid was dissloved in 5 ml of water, while 0.5 g of each composition comprising 40% or less of the same was dissloved or dispersed in an oil or fat followed by adding 5 ml of water thereto. With the use of each aqueous composition thus obtained, 50 g of corn salad oil and 56 g of "Koikuchi" soy sauce, an emulsion of the corn salad oil and the soy sauce was obtained in the same manner as the one described in Example 31. Then the emulsion was introduced into a glass cylinder and stored in an incubator while periodically changing the temperature at 20° C. for 12 hours and at 35° C. for 12 hours.

As a result, an oily phase immediately separated from an aqueous phase in the case of the composition comprising the glycerol fatty acid monoester alone.

2% of an oily phase separated out after 15 days in the case of the composition comprising the glycerol fatty acid ester and phosphatide at a ratio of 50/50. On the other hand, no separation was observed in the cases of those comprising the two materials at ratios of 30/70 to 10/90.

(4) Dispersion test on fine inorganic particles

With the use of a 0.2% aqueous solution of each composition, the dispersibilities of a titanium white pigment and highly fine grains of calcium carbonate were determined in the same manner as the one described in Example 31.

In the cases of the compositions comprising the glycerol fatty acid ester and phosphatide at ratios of 10/90 to 50/50, to which no saline solution was added, the titanium white pigment showed scarcely any precipitation. In the cases of those comprising the same at ratios of 60/40 to 90/10, stable dispersion was observed although precipitation slowly proceeded. When the saline solution was added, no change was observed in the former cases while the dispersabilities were slowly lowered in the latter cases.

In the cases of the composition comprising the glycerol fatty acid ester and phosphatide at ratios of 10/90 to 80/20, to which no saline solution was added, the highly fine grains of calcium carbonate showed excellent dispersion after two hours. When the saline solution was added thereto, a slight decrease in the dispersabilities was observed in those comprising the same at ratios of 60/40 to 80/20.

(5) $\beta$-Carotene solubilizaton test

With the use of a 1% aqueous solution of each composition, $\beta$-carotene was solubilized in the same manner as the one described in Example 31.

As a result, the composition comprising the phosphatide alone showed an absorbance at 455 nm of 0.924. On the other hand, those comprising the glycerol fatty acid ester and phosphatide at ratios of 20/80 and 30/70 showed absorbances of 0.763 and 0.529, respectively.

EXAMPLE 33

Mono acyl glycero phospholipid B and a distilled glycerol monoester of unsaturated fatty acids (Emulsy MO mfd. by Riken Vitamin Co., Ltd.; mainly comprising linoleic acid and having an iodine value of 76) were dissloved in ethanol in the same manner as the one described in Example 32. After distilling off the ethanol in vacuo, a semisolid composition was obtained.

(1) Emulsification stability test on corn salad oil and soy sauce

With the use of each composition, an emulsion of corn salad oil and "Koikuchi" soy sauce was prepared in the same manner as the one described in Example 32. The obtained emulsion was introduced into a glass clyinder and stored in an incubator while periodically changing the temperature, i.e., at 20° C. for 12 hours and at 35° C. for 12 hours.

As a result, an oily phase immediately separated from an aqueous phase in the case of the composition comprising the glycerol fatty acid monoester alone.

In the cases of the compositions comprising the glycerol fatty acid ester and phosphatide at ratios of 70/30 to 50/50, the stabilities gradually increased. In the case of that comprising the materials at a ratio of 50/50, 2% of an oily phase separated out after 30 days. On the other hand, no separation was observed after 30 days in the cases of those comprising the same at ratios of 30/70 to 10/90.

(2) Emulsification stability test on corn salad oil and orange juice

The procedure as described in Example 31 with regard to the emulsification stability test on corn salad oil and soy sauce was followed except that the soy sauce was replaced by reconstituted orange juice (pH 3.5).

In the case of the composition comprising the glycerol fatty acid monoester alone, the emulsion was immediately broken and an oily phase separated out.

In contrast thereto, in the cases of those comprising the glycerol fatty acid ester and phosphatide at ratios of 70/30 to 50/50, the degree of separation of oily components gradually decreased. In the cases of those comprising the same at ratios of 50/50 to 10/90, scarcely any separation was observed.

EXAMPLE 34

With the use of mono acyl glycero phospholipid E and Emulsy MS, compositions were prepared in the same manner as the one described in Example 32.

(1) Acid- and salt-resistance test

To 1 g of each composition, water was added to give a volume of 100 ml. With the use of the aqueous solution thus obtained, the procedure of Example 31 was followed. As a result, the control, acidic and saline solutions of the composition comprising the phosphatide alone showed transmittance at 720 nm of 97%, 84% and 95%, respectively. On the other hand, the control, acidic and saline solutions of the composition comprising the glycerol fatty acid ester and phosphatide at a ratio of 20/80 showed transmittances of 99%, 98% and 93%, respectively. The control, acidic and saline solutions of that comprising the same at a ratio of 30/70 showed transmittances of 99%, 96% and 98%, respectively.

EXAMPLE 35

With the use of the mono acyl glycero phospholipid E and Emulsy MO, compositions were prepared in the same manner as the one described in Example 33.

(1) Acid- and salt-resistance test

With the use of a 0.5% aqueous solution of each composition, the procedure relating to the acidic solution of Example 31 was followed. As a result, the control and acidic solutions of the composition comprising the phosphatide alone showed transmittances at 720 nm of 97% and 84%, respectively. The control and acidic solutions of the composition comprising the glycerol fatty acid ester and phosphatide at a ratio of 10/90 showed transmittances of 99% and 92%, respectively. While the control and acidic solutions of that comprising the same at a ratio of 50/50 showed transmittances of 91% and 86%, respectively.

(2) Emulsification stability test on corn salad oil and soy sauce

An emulsification stability test on corn salad oil and soy sauce was carried out in the same manner as the one described in Example 33.

As a result, 4% of an oily phase separated out after 30 days in the case of the composition comprising the glycerol fatty acid ester and phosphatide at a ratio of 70/30. In contrast thereto, those comprising the same at ratios of 50/50 to 10/90 showed scarcely any separation, suggesting high stabilities.

(3) Emulsification stability test on corn salad oil and orange juice

An emulsification stability test on corn salad oil and reconstituted orange juice was carried out in the same manner as the one described in Example 33.

As a result, the emulsion was immediately broken in the case of the composition comprising the glycerol fatty acid ester alone.

2% of an oily phase separated out after 30 days in the case of the composition comprising the glycerol fatty acid ester and phosphatide at a ratio of 60/40. On the other hand, those comprising teh same at ratios of 50/50 to 10/90 showed scarcely any separation after 30 days, suggesting high stabilities.

EXAMPLE 36

Mono acyl glycero phospholipid J and Emulsy MS were mixed together both in the form of powders to give compositions of various weight ratios.

(1) Surface activity test

With the use of a 0.5% aqueous solution of each composition, the surface tension and permeability both at 30° C. were determined each in the same manner as the one described in Example 31. FIG. 2 shows the result.

EXAMPLE 37

Mono acyl glycero phospholipid K and Emulsy MS were blended together and dissloved in ethanol. After distilling off the ethanol in vacuo, compositions of various weight ratios were obtained.

(1) Surface activity test

With the use of a 0.5% aqueous solution of each composition, the surface tension at 25° C. was determined in the same manner as the one described in Example 31.

As a result, the composition comprising the phosphatide alone showed a surface tension of 36.4 dyne/cm. On the other hand, those comprising the glycerol fatty acid ester and phosphatide at ratios of 10/90, 20/80, 30/70, 40/60, 50/50, 60/40 and 70/30 showed surface tensions of 34.6 dyne/cm, 32.9 dyne/cm, 31.7 dyne/cm, 31.6 dyne/cm, 31.9 dyne/cm, 32.4 dyne/cm and 33.3 dyne/cm, respectively,

EXAMPLE 38

Mono acyl glycero phospholipid E was mixed with a glycerol fatty acid ester composition containing 88% of glycerol fatty acid monoesters, which was obtained by blending an undistilled glycerol fatty acid ester of hardened beef tallow (Sun Soft 2500 mfd. by Taiyo Kagaku Co., Ltd.) containing 51% of glycerol fatty acid monoesters with Emulsy MS at a ratio of 2:8, to obtain compositions in the same manner as the one described in Example 32.

(1) Acid- and salt-resistance test

Water was added to each composition to give a 1% aqueous solution. With the use of the obtained solution, the procedure of Example 31 was followed.

After cooling, the control and acidic solutions of the composition comprising the phosphatide alone showed transmittances at 720 nm of 97% and 84%, respectively.

The control and acidic solutions of the composition comprising the glycerol fatty acid ester and phosphatide at a ratio of 10/90 showed transmittances of 96% and 85%, respectively. The control and acidic solutions of that comprising the same at a ratio of 20/80 showed transmittances of 91% and 89%, respectively. The control and acidic solutions of that comprising the same at a ratio of 30/70 showed transmittances of 88% and 84%, respectively.

EXAMPLE 39

Seven parts by weight of mono acyl glycero phospholipid L and three parts by weight of Emulsy MS were blended and the mixture was heated in water to thereby give a 20% by weight aqueous paste. To 5 g of the obtained paste, water was added to give 200 ml of a solution. Then the surface tension of this solution was determined at 25° C. while the permeability thereof was determined according to the canvas disc method at 25° C. as described in Example 31. As a result, it showed a surface tension of 29.8 dyne/cm and a permeation period of 7 minutes and 17 seconds. When compared to the case of the composition comprising the phosphatide alone, i.e., having a surface tension of 33.6 dyne/cm and a permeation period of 12 minutes and 45 seconds, an improvement was observed.

EXAMPLE 40

Mono acyl glycero phospholipid M and Emulsy MS were mixed together to give compositions in the same manner as the one described in Example 33.

Water was added to each composition to give a 0.5% aqueous solution. Then the acid-resistance of the obtained solution was determined in the same manner as the one described in Example 31.

After cooling, the control and acidic solutions of the composition comprising the glycerol fatty acid ester and phosphatide at a ratio of 10/90 showed transmittances of 67% and 68%, respectively, while the control and acidic solutions of that comprising the same at a ratio of 20/80 showed transmittances of 60% and 61%, respectively.

EFFECT OF THE INVENTION

The effect of the present invention consists in an improvement in the disadvantages of polyglycerol fatty acid esters, sucrose fatty acid esters, sorbitan fatty acid esters and glycerol fatty acid monoesters and a provision of a surfactant composition at a low price.

BRIEF DESCRIPTION OF THE DRAWINGS

FIG. 1 shows the results of the surface activity test of Example 31, while

Figure 1:
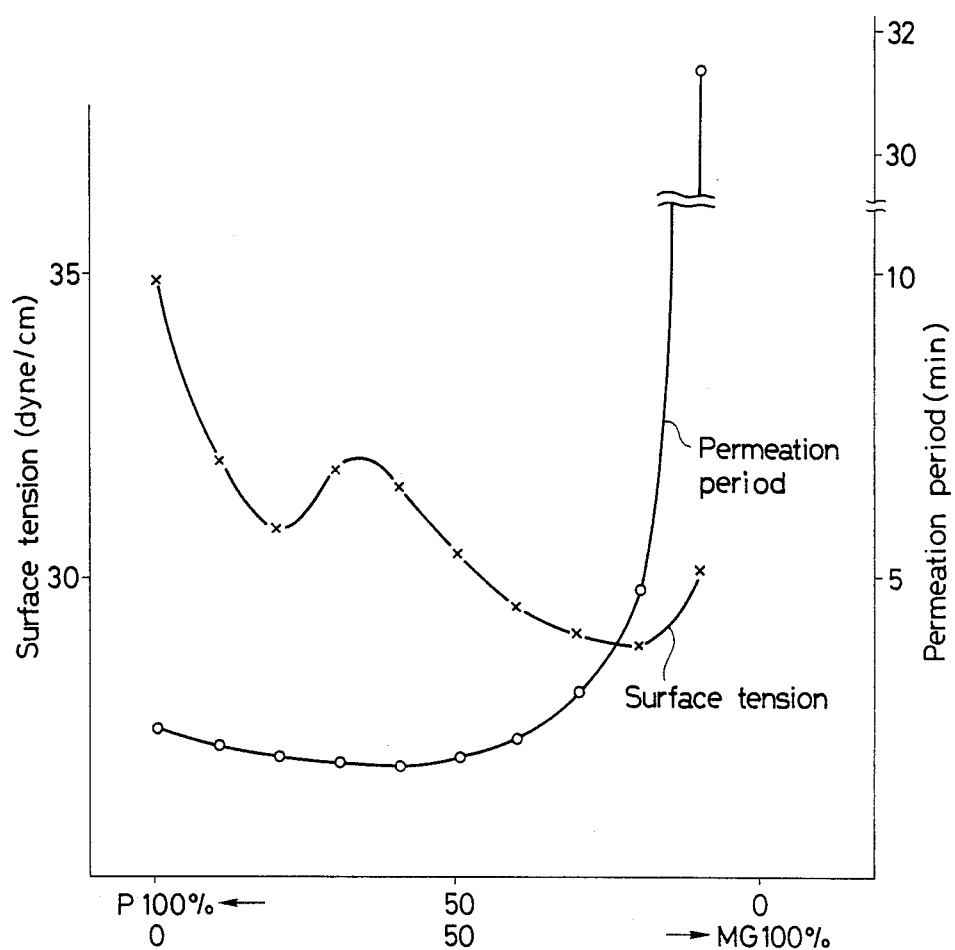
Figure 2:
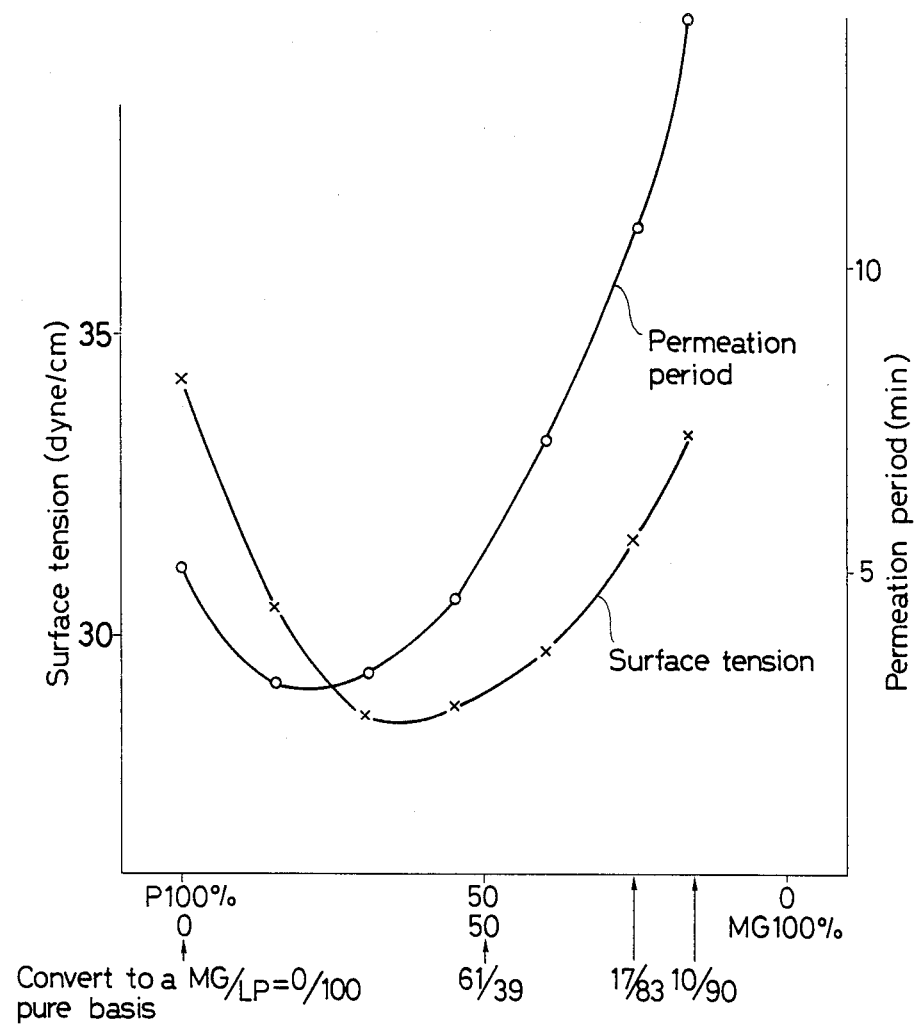
FIG. 2 shows the results of the surface activity test of Example 36.

What is claimed is:

1. A surfactant composition which comprises:
partially deacylated glycerophospholipid(s) which comprises at least 40% by weight of (A) monoacylglycerophospholipid(s) and
one or more (B) compounds selected from the group consisting of polyglycerol fatty acid esters, sucrose fatty acid esters, sorbitan fatty acid esters and glycerol fatty acid monoesters,
and wherein said (B) compound(s) and said (A) monoacylglycerophospholipid(s) in said partially deacylated glycerophospholipid(s) are blended at a ratio of 10/90 to 95/5 on a weight basis.

2. A surfactant composition as set forth in claim 1, wherein said compound(s) selected from the group consisting of polyglycerol fatty acid esters, sucrose fatty acid esters, sorbitan fatty acid esters and glycerol fatty acid monoesters are selected from among mono- di- and polyesters of saturated and/or unsaturated fatty acids having 12 to 22 carbon atoms with polyglycerol, sucrose, glycerol and polyols selected from among sorbitol, sorbitan and sorbide.

3. A surfactant composition as set forth in claim 1, wherein said (A) monoacylglycerophospholipid(s) comprises mono acyl phosphatidylcholine as the main component and simultaneously contains mono acyl phosphatidylethanolamine as well as one or more monoacylglycerophospholipids selected from the group consisting of mono acyl phosphatidylinositol, mono acyl phosphatidic acid and mono acyl phosphatidylserine.

4. A surfactant composition as set forth in claim 3, wherein said (A) monoacylglycerophospholipid(s) substantially comprises mono acyl phosphatidylcholine.

5. A surfactant composition as set forth in claim 2, wherein said polyglycerol fatty acid ester(s) are selected form the group consisting of mono- di- and polyesters of polyglycerol having a degree of polymerization of 4 or above wiht saturated and/or unsaturated fatty acids having 12 to 22 carbon atoms.

6. A surfactant composition as set forth in claim 1, wherein said (B) compounds are polyglycerol fatty acid esters, and said ratio of said (B) compound(s) and said (A) monoacylglycerophospholipid(s) in said partially deacylated glycerophospholipid(s) is 40/60 to 95/5 on a weight basis.

7. A surfactant composition as set forth in claim 6, wherein said polyglycerol fatty acid esters are polyglycerol fatty acid esters which have an HLB of 11 or above.

8. A surfactant composition as set forth in claim 1, wherein said (B) compounds are compounds selected from the group consisting of polyglycerol fatty acid esters and sucrose fatty acid esters, and said ratio of said (B) compound(s) and said (A) monoacylglycerophospholipid(s) in said partially deacylated glycerophospholipid(s) is 40/60 to 90/10 on a weight basis.

9. A surfactant composition as set forth in claim 8, wherein said polyglycerol fatty acid esters are polyglycerol fatty acid esters which have an HLB of less than 11.

10. A surfactant composition as set forth in claim 1, wherein said (B) compounds are sorbitan fatty acid esters, and said ratio of said (B) compounds and said (A) monoacylglycerophospholipid(s) in said partially deacylated glycerophospholipid(s) is 40/60 to 80/20 on a weight basis.

11. A surfactant composition as set forth in claim 1, wherein said (B) compounds are glycero fatty acid monoesters, and said ratio of said (B) compound(s) and said (A) monoacylglycerophospholipid(s) in said partially deacylated glycerophospholipid(s) is 10/90 to 90/10 on a weight basis.

* * * * *